(12) United States Patent
Holland

(10) Patent No.: US 9,943,646 B2
(45) Date of Patent: Apr. 17, 2018

(54) SAFETY SYRINGE

(71) Applicant: OWEN MUMFORD LTD, Oxfordshire (GB)

(72) Inventor: Damian Alexander Holland, Oxfordshire (GB)

(73) Assignee: Owen Mumford Ltd., Oxfordshire (GB)

( * ) Notice: Subject to any disclaimer, the term of this patent is extended or adjusted under 35 U.S.C. 154(b) by 0 days.

(21) Appl. No.: 15/322,954

(22) PCT Filed: Aug. 21, 2015

(86) PCT No.: PCT/EP2015/069212
§ 371 (c)(1),
(2) Date: Dec. 29, 2016

(87) PCT Pub. No.: WO2016/026952
PCT Pub. Date: Feb. 25, 2016

(65) Prior Publication Data
US 2017/0165423 A1    Jun. 15, 2017

(30) Foreign Application Priority Data

Aug. 21, 2014 (GB) .................................. 1414911.6
Nov. 28, 2014 (GB) .................................. 1421187.4
May 13, 2015 (GB) .................................. 1508153.2

(51) Int. Cl.
*A61M 5/00* (2006.01)
*A61M 5/178* (2006.01)
(Continued)

(52) U.S. Cl.
CPC ............ *A61M 5/178* (2013.01); *A61M 5/315* (2013.01); *A61M 5/31501* (2013.01);
(Continued)

(58) Field of Classification Search
CPC .. A61M 5/178; A61M 5/3243; A61M 5/3257; A61M 5/326; A61M 5/315;
(Continued)

(56) References Cited

U.S. PATENT DOCUMENTS 5,163,918 A    11/1992  Righi et al.
5,300,030 A *   4/1994  Crossman ........... A61M 5/2033
                                                    604/134

(Continued)

FOREIGN PATENT DOCUMENTS

AU    2014203206 A1    7/2014
DE      10156959 A1    2/2003
(Continued)

OTHER PUBLICATIONS

International Search Report, dated Nov. 3, 2015, from corresponding PCT application No. PCT/EP2015/069212.

(Continued)

*Primary Examiner* — Kevin C Sirmons
*Assistant Examiner* — Leah Swanson
(74) *Attorney, Agent, or Firm* — Young & Thompson

(57) ABSTRACT

A safety syringe (100; 700; 1200) comprising: a barrel (104; 704; 1204) having an opening at an end thereof; a syringe plunger (108; 708; 1208) configured to move within the barrel such that an inward stroke of the syringe plunger causes a substance within the barrel to be expelled from the opening; and a sheath (112; 712; 1212) configured to cover at least partially the opening in the barrel after use of the syringe, wherein the sheath is coupled to the syringe plunger and is configured to decouple from the syringe plunger at a point on the inward stroke such that the sheath is moveable independently of the syringe plunger and further movement of the sheath after decoupling at least partially covers the opening in the barrel.

21 Claims, 17 Drawing Sheets

(51) Int. Cl.
*A61M 5/315* (2006.01)
*A61M 5/32* (2006.01)
*A61M 5/50* (2006.01)

(52) U.S. Cl.
CPC ........ *A61M 5/31511* (2013.01); *A61M 5/326* (2013.01); *A61M 5/3243* (2013.01); *A61M 5/3257* (2013.01); *A61M 5/5066* (2013.01); *A61M 2005/3265* (2013.01)

(58) Field of Classification Search
CPC .......... A61M 5/31501; A61M 5/31511; A61M 5/3271; A61M 5/3272; A61M 5/3275; A61M 5/5066; A61M 2005/3252; A61M 2005/3254; A61M 2005/3261; A61M 2005/3264; A61M 2005/3265
See application file for complete search history.

(56) References Cited

U.S. PATENT DOCUMENTS

| | | | |
|---|---|---|---|
| 5,368,568 | A | 11/1994 | Pitts et al. |
| 5,370,628 | A | 12/1994 | Allison et al. |
| 5,460,611 | A | 10/1995 | Alexander |
| 5,514,107 | A | 5/1996 | Haber et al. |
| 5,591,138 | A | 1/1997 | Vaillancourt |
| 5,713,871 | A | 2/1998 | Stock |
| 5,843,047 | A | 12/1998 | Pyrozyk et al. |
| 5,893,845 | A | 4/1999 | Newby et al. |
| 5,989,226 | A | 11/1999 | Hymanson |
| 6,110,147 | A | 8/2000 | Perouse |
| 6,319,234 | B1 * | 11/2001 | Restelli ................ A61M 5/326 604/110 |
| 6,461,333 | B1 | 10/2002 | Frezza |
| 6,511,460 | B1 | 1/2003 | Arnissolle |
| 6,626,863 | B1 | 9/2003 | Berler |
| 6,629,957 | B1 | 10/2003 | Wiklund |
| 6,918,889 | B1 | 7/2005 | Brunel |
| 2001/0037089 | A1 | 11/2001 | Domici, Jr. |
| 2001/0037090 | A1 | 11/2001 | Cherif-Cheikh |
| 2002/0045864 | A1 | 4/2002 | Perez et al. |
| 2002/0099338 | A1 | 7/2002 | Young |
| 2003/0144631 | A1 | 7/2003 | Doyle et al. |
| 2003/0187401 | A1 | 10/2003 | Doyle |
| 2004/0167476 | A1 | 8/2004 | Westbye |
| 2006/0111675 | A1 | 5/2006 | Millerd |
| 2006/0264887 | A1 | 11/2006 | Lande |
| 2007/0060896 | A1 * | 3/2007 | Miller ................ A61M 5/31511 604/222 |
| 2008/0097337 | A1 | 4/2008 | Judd et al. |
| 2008/0306450 | A1 | 12/2008 | Martin |
| 2009/0187150 | A1 | 7/2009 | Ferland et al. |
| 2010/0185178 | A1 * | 7/2010 | Sharp .................... A61M 5/002 604/506 |
| 2010/0286611 | A1 | 11/2010 | Schraga |
| 2011/0066114 | A1 | 3/2011 | McDown et al. |
| 2012/0046615 | A1 | 2/2012 | Koiwai et al. |
| 2012/0136316 | A1 | 5/2012 | Davies et al. |
| 2012/0143146 | A1 * | 6/2012 | Strehl ................ A61M 5/31511 604/208 |
| 2013/0066271 | A1 | 3/2013 | West |
| 2013/0110043 | A1 | 5/2013 | Levin |
| 2013/0138046 | A1 | 5/2013 | Feng |
| 2013/0144255 | A1 | 6/2013 | Cohn |
| 2015/0032061 | A1 | 1/2015 | Jakob et al. |

FOREIGN PATENT DOCUMENTS

| | | |
|---|---|---|
| DE | 102010008806 A1 | 8/2011 |
| EP | 0774268 A1 | 5/1997 |
| EP | 1079878 A1 | 3/2001 |
| EP | 1421964 A2 | 5/2004 |
| EP | 2752211 A1 | 7/2014 |
| JP | 3068710 U | 2/2000 |
| JP | 2002-165880 A | 6/2002 |
| JP | 2003-79726 A | 3/2003 |
| JP | 2003-220142 A | 8/2003 |
| JP | 2004-148091 A | 5/2004 |
| JP | 2006-263444 | 10/2006 |
| JP | 2008-73519 A | 4/2008 |
| JP | 2009-77943 A | 4/2009 |
| JP | 2009-261589 A | 11/2009 |
| PL | 196932 B1 | 2/2008 |
| WO | 99/22791 A1 | 5/1999 |
| WO | 01/80931 A2 | 11/2001 |
| WO | 2006/124947 A1 | 11/2006 |
| WO | 2007/099367 A1 | 9/2007 |

OTHER PUBLICATIONS

GB Search Report, dated Mar. 6, 2015, from corresponding GB application No. 1414911.6.
GB Search Report, dated Mar. 6, 2015, from corresponding GB application No. 1421187.4.
GB Search Report, dated Nov. 19, 2015, from corresponding GB application No. 1508153.2.
Subject Matter Search Report, dated Feb. 24, 2015.

* cited by examiner

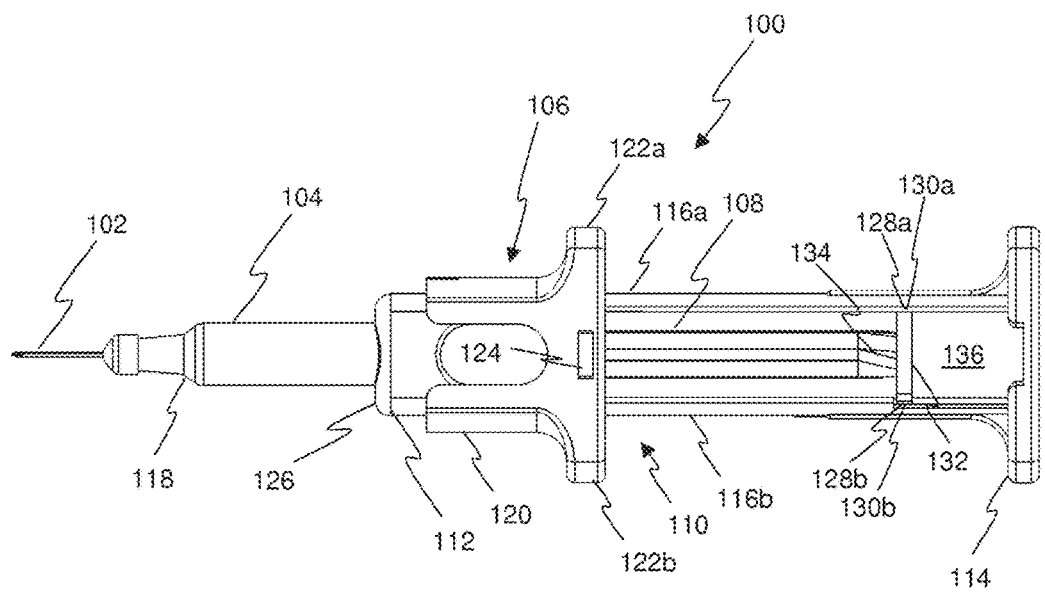
Fig. 1
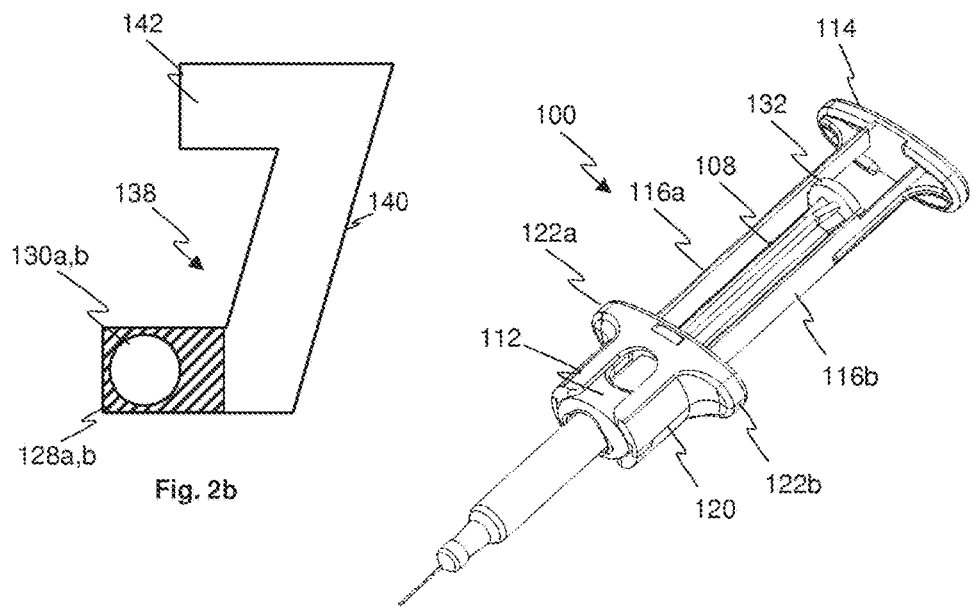
Fig. 2b
Fig. 2a

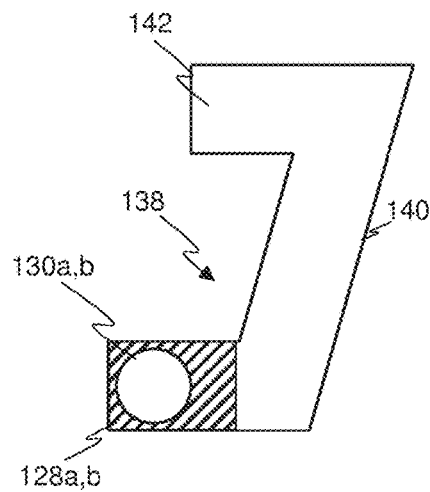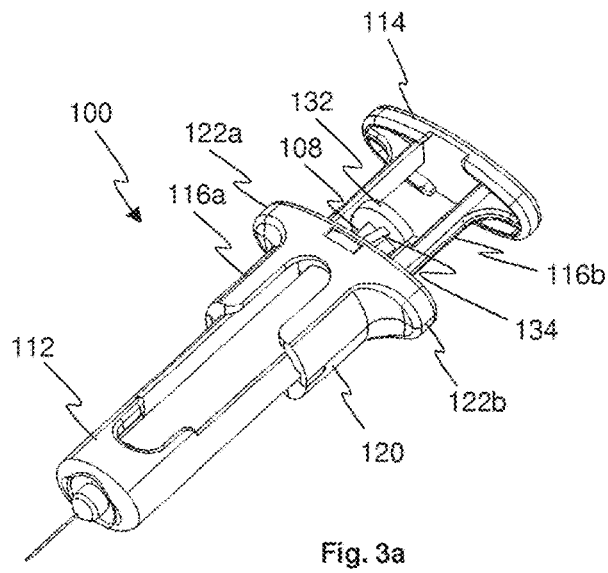
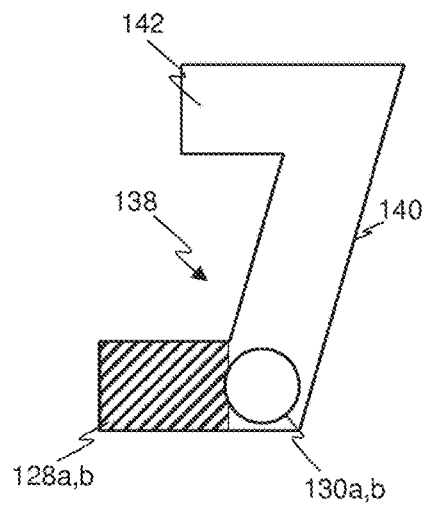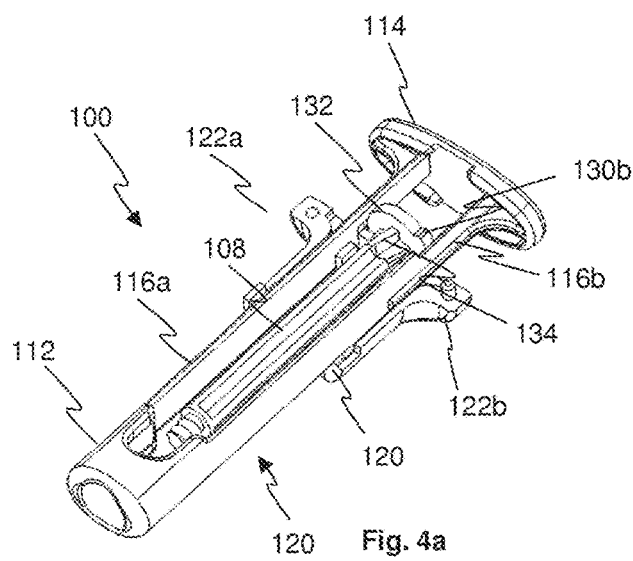

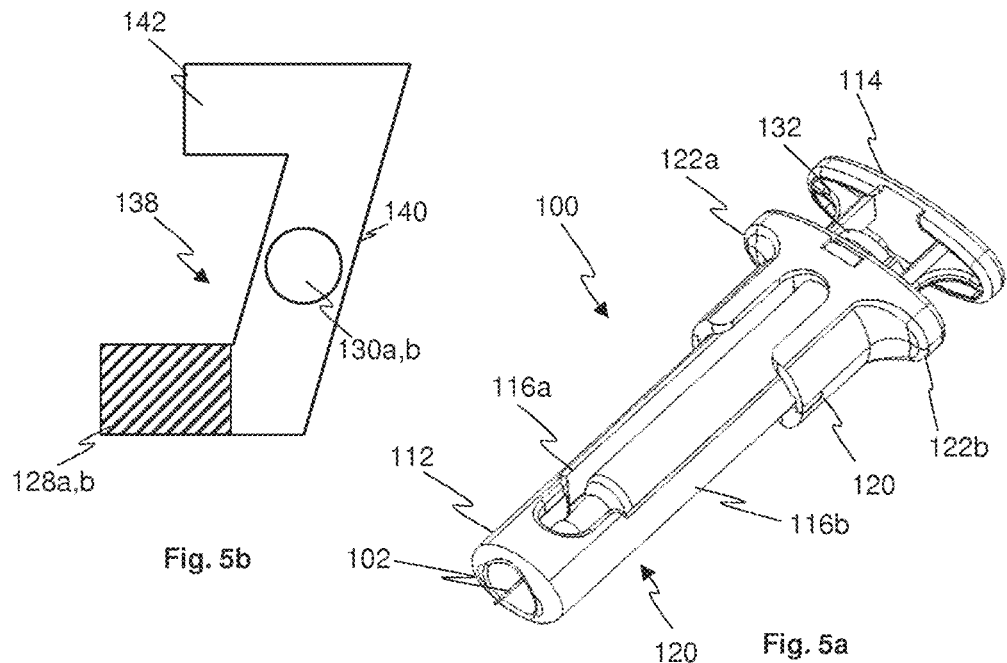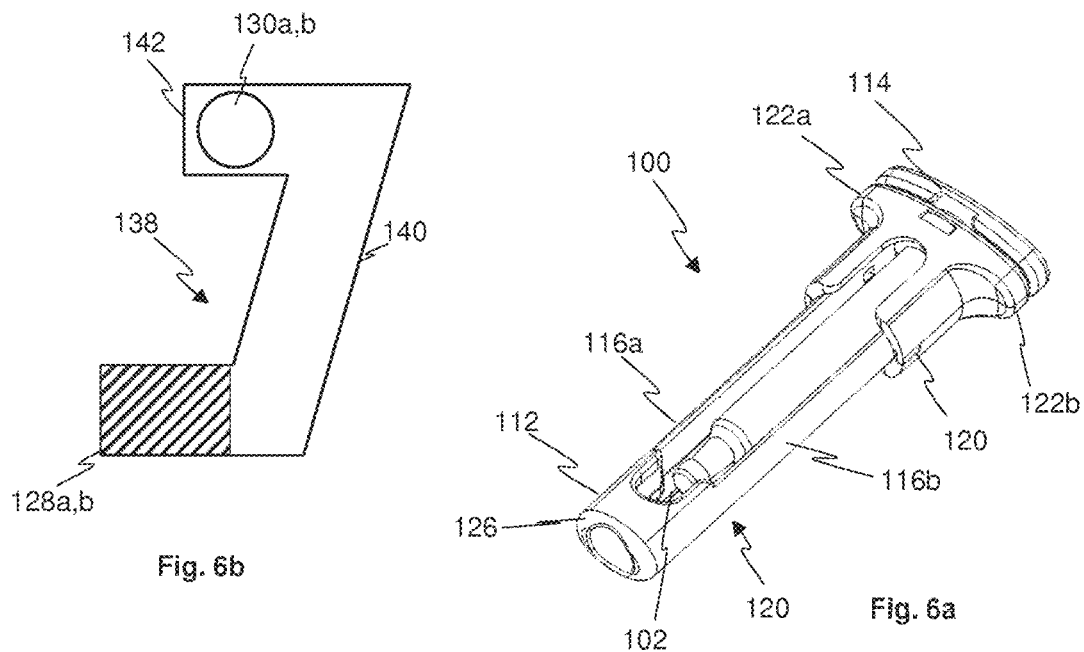

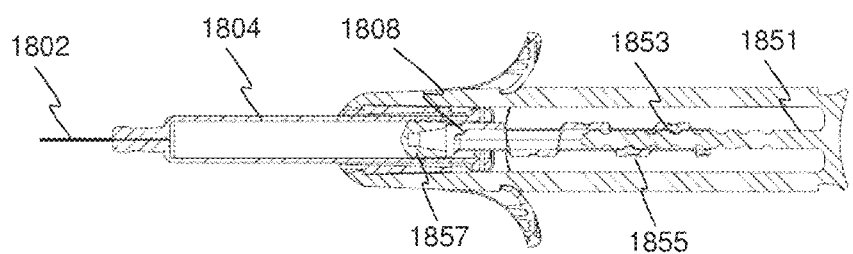
(a)
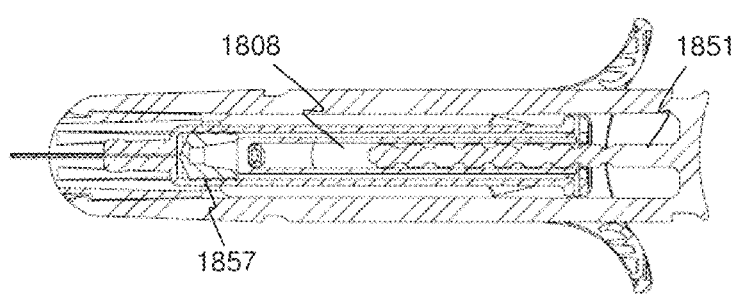
(b)
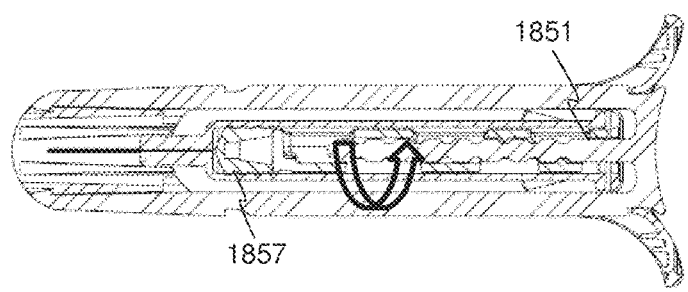
(c)
Fig. 19

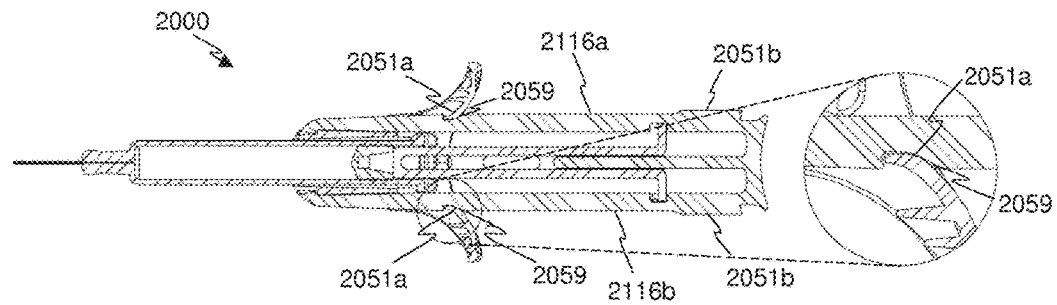
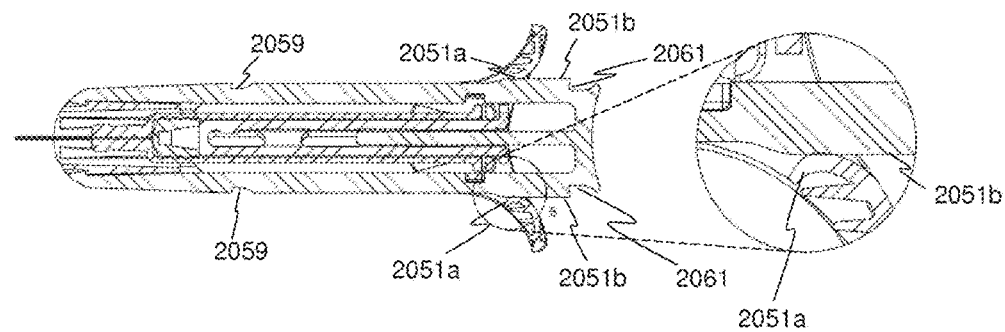
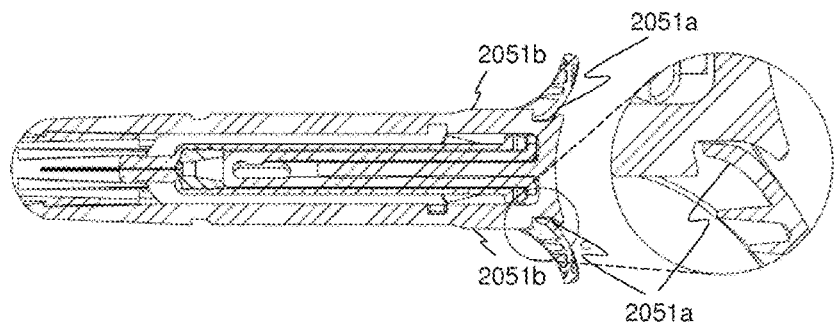
Fig. 22

SAFETY SYRINGE

TECHNICAL FIELD

The invention relates to safety syringes and devices for fitting to syringes to convert them to safety syringes. In particular embodiments, the invention relates to, but is not limited to, passive safety syringes and associated devices.

BACKGROUND

Broadly, syringes comprise a barrel having a hypodermic needle at one end and a plunger configured to move within the barrel such that an inward stroke of the plunger causes a substance contained within the barrel to be expelled from the needle.

Safety syringes typically include some form of safety mechanism to protect healthcare workers from the hypodermic needle after it has been injected into a patient. Exemplary safety syringes may include a sheath for covering the needle, or may cause the needle to retract within the barrel of the syringe.

Safety syringes may be broadly split into 'active' and 'passive'. Active safety syringes typically require some action by a user of the syringe to engage the safety mechanism.

Such action may be taken after removal of the needle from the patient, or may be taken during removal of the needle from the patient. Typically, the action required to engage the safety mechanism is separate from the action required to cause the inward stroke of the plunger. Passive safety syringes typically engage the safety mechanism without any specific action by the user, that is, without any action other than that usually taken to use the syringe.

Known safety syringes comprise a spring-loaded safety mechanism that may be engaged by the healthcare worker after the inward stroke of the plunger. The spring force urges a surface against the skin of the patient, thereby extracting the needle and simultaneously engaging the safety mechanism. Such devices are prone to misuse as the spring-loaded mechanism causes discomfort and bruising to patients when it is activated. Therefore, healthcare workers are known to remove the needle from the patient before engaging the safety mechanism. This exposes the healthcare worker to the needle after use and the spring-loaded action of the safety mechanism may lead to blood splatter from the needle.

Other known safety syringes require the needle to be removed from the patient before the safety mechanism may be engaged. This exposes the healthcare worker to the needle after use.

SUMMARY

According to the invention in one aspect, there is provided a safety syringe comprising: a barrel having an opening at an end thereof; a syringe plunger configured to move within the barrel such that an inward stroke of the syringe plunger causes a substance within the barrel to be expelled from the opening; and a sheath configured to cover at least partially the opening in the barrel after use of the syringe, wherein the sheath is coupled to the syringe plunger and is configured to decouple from the syringe plunger at a point on the inward stroke such that the sheath is moveable independently of the syringe plunger and further movement of the sheath after decoupling at least partially covers the opening in the barrel.

Optionally, the sheath is configured to move along an exterior of the barrel during the inward stroke of the syringe plunger and to decouple from the syringe plunger at or before a point at which the sheath passes of the opening in the barrel.

Optionally, the point on the inward stroke of the syringe plunger is the end of the inward stroke of the syringe plunger.

Optionally, the safety syringe further comprises a decoupling mechanism configured to decouple the sheath and the syringe plunger by way of the force applied to the syringe plunger on its inward stroke.

Optionally, the sheath forms part of a safety plunger and wherein the decoupling mechanism comprises a lug on the syringe plunger configured to move between engagement and disengagement with a coupling recess in the safety plunger.

Optionally, the lug of the syringe plunger is configured to disengage from the coupling recess of the safety plunger by rotation of the syringe plunger relative to the safety plunger.

Optionally, the body of the syringe plunger comprises a rotation surface configured to engage with a reaction surface to rotate the plunger, wherein the reaction surface is fixed with respect to the barrel.

Optionally, the safety syringe further comprises a locking mechanism configured to lock the sheath in a position at least partially covering the opening of the barrel.

Optionally, the lug is configured to engage with a return recess in the safety plunger at the end of the inward stroke of the safety plunger.

Optionally, the safety syringe further comprises a resiliently deformable syringe plunger tip configured to compress against an internal surface of the barrel proximal an end comprising the opening, thereby providing a biasing force urging the syringe plunger outward.

Optionally, the syringe plunger is configured such that the biasing force causes outward movement and reverse rotation of the syringe plunger to move the lug into the return recess.

Optionally, the lateral extent of the return recess is less than the lateral extent of the coupling recess preventing full reverse rotation of the syringe plunger.

Optionally, the safety syringe comprises a locking channel comprising the coupling recess and the return recess connected by a substantially longitudinal channel, and wherein the locking channel is configured to guide the lug during activation of the locking mechanism.

Optionally, the lug is configured to meet an end of the substantially longitudinal channel at the end of the inward stroke of the safety plunger, thereby compressing the resiliently deformable tip of the syringe plunger.

Optionally, the safety plunger extends beyond a head of the syringe plunger and a head of the safety plunger is connected to the sheath by at least one arm, the head for applying force by a user to cause the inward stroke of the safety plunger.

Optionally, the syringe further comprises a guard positioned between the head of the syringe plunger and the head of the safety plunger.

Optionally, the guard comprises a rod extending between the head of the safety plunger and the head of the syringe plunger, wherein the rod is configured to enter the syringe plunger after decoupling of the sheath and the syringe plunger.

Optionally, the safety syringe further comprises a hypodermic needle connected to the opening in the barrel, and wherein the sheath is configured to cover at least partially the hypodermic needle after use of the syringe. The safety syringe may be a cannula or other form of syringe not including a needle.

According to the invention in a further aspect, there is provided a sheath for use with a syringe, the syringe comprising a barrel having an opening at an end thereof and a syringe plunger configured to move within the barrel such that an inward stroke of the syringe plunger causes a substance within the barrel to be expelled from the opening, wherein the sheath is coupled to the syringe plunger and comprises a decoupling means for decoupling the sheath from the syringe plunger at a point on the inward stroke such that the sheath is moveable independently of the syringe plunger and further movement of the sheath after decoupling at least partially covers the opening in the barrel.

According to the invention in a further aspect, there is provided a safety syringe comprising: a barrel having an opening at an end thereof; a syringe plunger configured to move within the barrel to cause a substance within the barrel to be expelled from the opening; a safety plunger coupled to the syringe plunger such that an inward stroke of the safety plunger causes the syringe plunger to move within the barrel; and a sheath configured to cover at least partially the opening in the barrel after use of the syringe, wherein the safety plunger is configured to couple to the sheath at a first point on the inward stroke and is configured to decouple from the syringe plunger at a second point on the inward stroke such that the safety plunger is moveable independently of the syringe plunger, and wherein further movement of the safety plunger after the first and second points on the inward stroke causes the sheath at least partially to cover the opening in the barrel.

Optionally, the first point on the inward stroke is the outermost point on the inward stroke, such that the safety plunger is coupled to the syringe plunger at the beginning of the inward stroke.

Optionally, the sheath is fixedly coupled to the safety plunger.

Optionally, the first point on the inward stroke is one of: before the second point on the inward stroke; after the second point on the inward stroke; and at substantially the same location as the second point on the inward stroke.

Optionally, the sheath comprises a sheath retaining means configured to fix the sheath with respect to the barrel, and operable to be released to allow movement of the sheath with respect to the barrel.

Optionally, the safety plunger is configured to release the retaining mechanism at a third point on the inward stroke.

Optionally, the safety syringe further comprises a coupling locking means for locking the safety plunger and the sheath in a coupled configuration.

Optionally, the safety plunger is configured to move along an exterior of the barrel during its inward stroke and to decouple from the syringe plunger at or before a point at which the sheath passes the opening in the barrel.

Optionally, the second point on the inward stroke is substantially the point at which the syringe plunger has reached the end of the barrel.

Optionally, the safety syringe further comprises a decoupling mechanism configured to decouple the safety plunger and the syringe plunger.

Optionally, the decoupling mechanism is configured to decouple the safety plunger and the syringe plunger under rotation of the syringe plunger relative to the safety plunger.

Optionally, the decoupling mechanism is configured to decouple the safety plunger and the syringe plunger by way of the force applied to the safety plunger on its inward stroke.

Optionally, the decoupling mechanism comprises a lug on the syringe plunger configured to move between engagement and disengagement with a coupling recess in the safety plunger.

Optionally, the lug of the syringe plunger is configured to disengage from the coupling recess of the safety plunger by rotation of the syringe plunger relative to the safety plunger.

Optionally, a body of the syringe plunger comprises a rotation surface configured to engage with a reaction surface to rotate the plunger, wherein the reaction surface is fixed with respect to the barrel.

Optionally, the safety syringe further comprises a locking mechanism configured to lock the sheath in a position at least partially covering the opening of the barrel.

Optionally, the locking mechanism comprises the lug and a return recess in the safety plunger, wherein the lug is configured to engage with the return recess at the end of the inward stroke of the safety plunger.

Optionally, the locking mechanism is a biased locking mechanism, the safety syringe further comprising a biasing member configured to provide a biasing force causing outward movement and reverse rotation of the syringe plunger to move the lug into the return recess.

Optionally, the biasing member comprises a resiliently deformable syringe plunger tip configured to compress against an internal surface of the barrel proximal an end comprising the opening.

Optionally, the lateral extent of the return recess is less than the lateral extent of the coupling recess, for preventing full reverse rotation of the syringe plunger.

Optionally, the safety syringe comprises a locking channel comprising the coupling recess and the return recess connected by a substantially longitudinal channel, and wherein the locking channel is configured to guide the lug during activation of the biased locking mechanism.

Optionally, the lug is configured to meet an end of the substantially longitudinal channel after the end of the inward stroke of the safety plunger, thereby compressing the resiliently deformable tip of the syringe plunger.

Optionally, the locking mechanism comprises a projection configured to enter a locking recess, wherein one of the projection and the locking recess is fixed in relation to the barrel and the other of the projection and the locking recess is located on the safety plunger or the sheath such that when the projection is located within the locking recess, the sheath is locked in a position at least partially covering the opening of the barrel.

Optionally, the projection is biased towards the locking recess such that the projection is urged into the locking recess upon alignment of the projection and the locking recess.

Optionally, during at least part of the inward stroke of the safety plunger, the projection is configured to ride over a surface until the projection and the locking recess are aligned, and wherein the biasing of the projection towards the locking recess exerts a frictional force on the safety plunger during the inward stroke.

Optionally, the projection comprises a resiliently deformable prong.

Optionally, the safety syringe comprises a rate controlling means for limiting and/or controlling a rate of travel of the safety plunger after the second point on the inward stroke.

Optionally, the rate controlling means comprises a rate limiting member, coupled to the safety plunger and configured to engage with the syringe plunger after the second point on the inward stroke.

Optionally, the rate limiting member comprises a first screw thread and the syringe plunger comprises a second screw thread that is configured to engage with the first screw thread to rotate the syringe plunger on further movement of the safety plunger after the second point on the inward stroke.

Optionally, the safety syringe further comprises a rotation prevention member configured to prevent rotation of the syringe plunger from the first to the second points on the inward stroke.

Optionally, the rotation prevention member comprises an aperture through which the syringe plunger passes, wherein the aperture comprises first keying features configured to correspond to second keying features on the syringe plunger.

Optionally, the syringe plunger is configured such that the second keying features disengage from the first keying features at the second point along the inward stroke.

Optionally, the syringe plunger is configured to pass through the aperture completely at the second point on the inward stroke.

Optionally, the safety syringe further comprises a resiliently deformable bung within the barrel.

Optionally, the resiliently deformable bung is configured to rotate when the syringe plunger rotates, and wherein the bung has a diameter greater than an inner diameter of the barrel, such that a friction force resists rotation of the bung and the syringe plunger.

Optionally, the resiliently deformable bung is configured to allow relative rotation between the resiliently deformable bung and the syringe plunger, and wherein a friction force between the syringe plunger and the resiliently deformable bung resists rotation of the bung and the syringe plunger.

Optionally, the rate controlling means comprises a resiliently deformable rate controlling projection configured to be deformed by a deforming surface after the second point on the inward stroke, thereby generating a friction force resisting further movement of the safety plunger.

Optionally, the resiliently deformable rate controlling projection projects radially inwardly towards a longitudinal axis of the safety syringe, and wherein the deforming surface is located on the safety plunger and comprises a tab extending outwardly away from the longitudinal axis of the safety syringe.

Optionally, the safety plunger extends beyond a head of the syringe plunger, and wherein a head of the safety plunger comprises at least one arm, the head of the safety plunger for applying force by a user to cause the inward stroke of the safety plunger.

Optionally, the safety syringe further comprises a guard positioned between the head of the syringe plunger and the head of the safety plunger.

Optionally, the guard comprises a rod extending between the head of the safety plunger and the head of the syringe plunger, wherein the rod is configured to enter the syringe plunger after decoupling of the safety plunger and the syringe plunger.

Optionally, the safety syringe further comprises a hypodermic needle connected to the opening in the barrel, and wherein the sheath is configured to cover at least partially the hypodermic needle after use of the syringe.

According to the invention in a further aspect, there is provided a safety syringe apparatus or use with a syringe, the syringe comprising a barrel having an opening at an end thereof and a syringe plunger configured to move within the barrel to cause a substance within the barrel to be expelled from the opening, wherein the safety syringe apparatus comprises: a safety plunger configured to be coupled to the syringe plunger such that an inward stroke of the safety plunger causes the syringe plunger to move within the barrel; and a sheath configured to cover at least partially the opening in the barrel after use of the syringe, wherein the safety plunger is configured to couple to the sheath at a first point on the inward stroke and is configured to decouple from the syringe plunger at a second point on the inward stroke such that the safety plunger is moveable independently of the syringe plunger, and wherein further movement of the safety plunger after the first and second points on the inward stroke causes the sheath at least partially to cover the opening in the barrel.

According to the invention in a further aspect, there is provided a kit of parts comprising: a safety plunger configured to be coupled to a syringe plunger of a syringe such that an inward stroke of the safety plunger causes the syringe plunger to move within the barrel; and a sheath configured to cover at least partially an opening in a barrel of the syringe after use of the syringe, wherein the safety plunger is configured to couple to the sheath at a first point on the inward stroke and is configured to decouple from the syringe plunger at a second point on the inward stroke such that the safety plunger is moveable independently of the syringe plunger, and wherein further movement of the safety plunger after the first and second points on the inward stroke causes the sheath at least partially to cover the opening in the barrel.

Optionally, the safety plunger is configured to be coupled to the sheath.

Optionally, the kit of parts further comprises a handle portion configured to be coupled to the barrel and to receive the safety plunger, such that the safety plunger is able to pass through the handle portion.

Optionally, the kit of parts further comprises a syringe.

According to the invention in a further aspect, there is provided a safety syringe comprising: a barrel having an opening at an end thereof; a syringe plunger configured to move within the barrel to cause a substance within the barrel to be expelled from the opening; a safety plunger coupled to the syringe plunger such that an inward stroke of the safety plunger causes the syringe plunger to move within the barrel; a sheath configured to cover at least partially the opening in the barrel after use of the syringe, wherein the safety plunger is configured to couple to the sheath at a first point on the inward stroke; a decoupling mechanism configured to decouple the safety plunger from the syringe plunger under rotation of the syringe plunger relative to the safety plunger at a second point on the inward stroke such that the safety plunger is moveable independently of the syringe plunger, wherein further movement of the safety plunger after the first and second points on the inward stroke causes the sheath at least partially to cover the opening in the barrel.

According to the invention in another aspect, there is provided a kit of parts comprising: a safety plunger; a syringe plunger, wherein the safety plunger is configured to be coupled to the syringe plunger such that an inward stroke of the safety plunger causes the syringe plunger to move within a barrel of a syringe; and a sheath configured to cover at least partially the opening in the barrel after use of the syringe, wherein, when the safety plunger, syringe plunger and the sheath are connected, the safety plunger is configured to couple to the sheath at a first point on the inward stroke and is configured to decouple from the syringe plunger at a second point on the inward stroke such that the safety plunger is moveable independently of the syringe plunger, and wherein further movement of the safety plunger after the first and second points on the inward stroke causes the sheath at least partially to cover the opening in the barrel.

Optionally, the kit of parts further comprises a handle portion configured to be connected to the safety plunger and to allow the safety plunger to pass through.

According to the invention in another aspect, there is provided a kit of parts comprising: a sub-assembly comprising a safety plunger and a syringe plunger, wherein the safety plunger is configured to be coupled to the syringe plunger such that an inward stroke of the safety plunger causes the syringe plunger to move within a barrel of a syringe; and a sheath configured to cover at least partially the opening in the barrel after use of the syringe, wherein, when the sub-assembly and the sheath are connected, the safety plunger is configured to couple to the sheath at a first point on the inward stroke and is configured to decouple from the syringe plunger at a second point on the inward stroke such that the safety plunger is moveable independently of the syringe plunger, and wherein further movement of the safety plunger after the first and second points on the inward stroke causes the sheath at least partially to cover the opening in the barrel. Optionally, the sub-assembly further comprises a handle portion configured to allow the safety plunger to pass through.

BRIEF DESCRIPTION OF THE DRAWINGS

FIG. 1 is a side elevation of a safety syringe with the plunger extended;

FIG. 2a is an isometric view of a safety syringe with the plunger extended;

FIG. 2b is a schematic view of a position of a locking mechanism corresponding to the position of the plunger in FIG. 2a;

FIG. 3a is an isometric view of a safety syringe with the plunger in a first position along its inward stroke;

FIG. 3b is a schematic view of a position of a locking mechanism corresponding to the position of the plunger in FIG. 3a;

FIG. 4a is an isometric view and partial section of a safety syringe with the plunger in a second position along its inward stroke;

FIG. 4b is a schematic view of a position of a locking mechanism corresponding to the position of the plunger in FIG. 4a;

FIG. 5a is an isometric view of a safety syringe with the plunger in a third position along its inward stroke;

FIG. 5b is a schematic view of a position of a locking mechanism corresponding to the position of the plunger in FIG. 5a;

FIG. 6a is an isometric view of a safety syringe with the plunger in a fourth position along its inward stroke;

FIG. 6b is a schematic view of a position of a locking mechanism corresponding to the position of the plunger in FIG. 6a;

FIG. 14a is an isometric view of a safety syringe with a plunger in a first position along its inward stroke;

FIG. 14b is a section through a sheath retaining means in a position corresponding to the position of the plunger in FIG. 14a;

FIG. 15a is an isometric view of a safety syringe with a plunger in a second position along its inward stroke;

FIG. 15b is a section through a sheath retaining means in a position corresponding to the position of the plunger in FIG. 15a;

FIG. 19a is a section through a safety syringe with a plunger in a first position along its inward stroke;

FIG. 19b is a section through a safety syringe with a plunger in a second position along its inward stroke;

FIG. 19c is a section through a safety syringe with a plunger at the end of its inward stroke;

FIG. 22a is a section through a safety syringe with a plunger in a first position along its inward stroke;

FIG. 22b is a section through a safety syringe with a plunger in a second position along its inward stroke; and FIG. 22c is a section through a safety syringe with a plunger at the end of its inward stroke.

DETAILED DESCRIPTION

Figure 7:
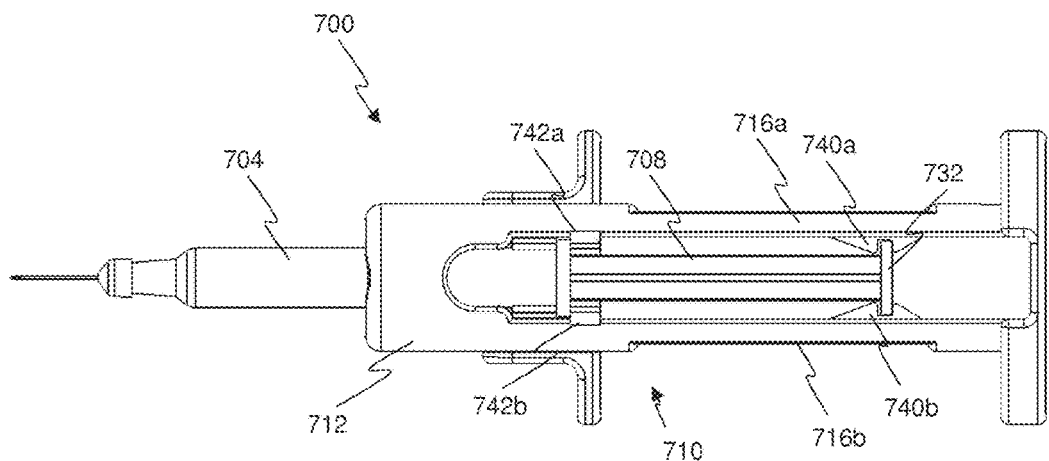
FIG. 7 is a side elevation of a safety syringe.

Generally, disclosed herein are safety syringes, methods of using safety syringes and safety syringe devices in which the sheath is moved into position at least partially covering a needle of the syringe under a force applied by the user. In exemplary safety syringes the sheath is coupled to the plunger and a force is applied by a user to the sheath thereby moving the plunger and the sheath together. At a point along the inward stroke of the plunger, the sheath decouples from the plunger and continued application of force by the user moves the sheath to a position at least partially covering the needle. A safety syringe device encompasses an apparatus configured to be fitted to a syringe in order to make the syringe a safety syringe. That is, exemplary safety syringe devices may be the same as the safety syringes described herein and shown in the figures with the barrel, needle and/or syringe plunger removed.

The 'inward stroke' is a stroke of a plunger longitudinal with respect to the syringe that is toward an open end of the barrel, that is, in a direction to expel a substance from the barrel. Outward has an opposite meaning.

Referring to FIG. 1, a safety syringe 100 comprises a hypodermic needle 102 fixed to an end of a barrel 104. The hypodermic needle is hollow. The barrel 104 comprises an opening at the point where the needle 102 is fixed to it such that a fluid path exists between the barrel 104 and the hollow channel of the needle 102. The syringe 100 further comprises a safety syringe apparatus comprising a handle portion 106 fixed in relation to the barrel 104, a safety plunger 110 and a sheath 112.

A syringe plunger 108 is positioned inside the barrel 104 and is configured to move therein. The syringe plunger 108 may move on an inward stroke wherein the syringe plunger 108 moves further into the barrel 104, or an outward stroke wherein the syringe plunger 108 is drawn out of the barrel 104. The syringe plunger 108 is configured such that the inward stroke causes a substance held in the barrel 104 to be expelled from the open end of the barrel 104 and through the needle 102.

Figure 14:
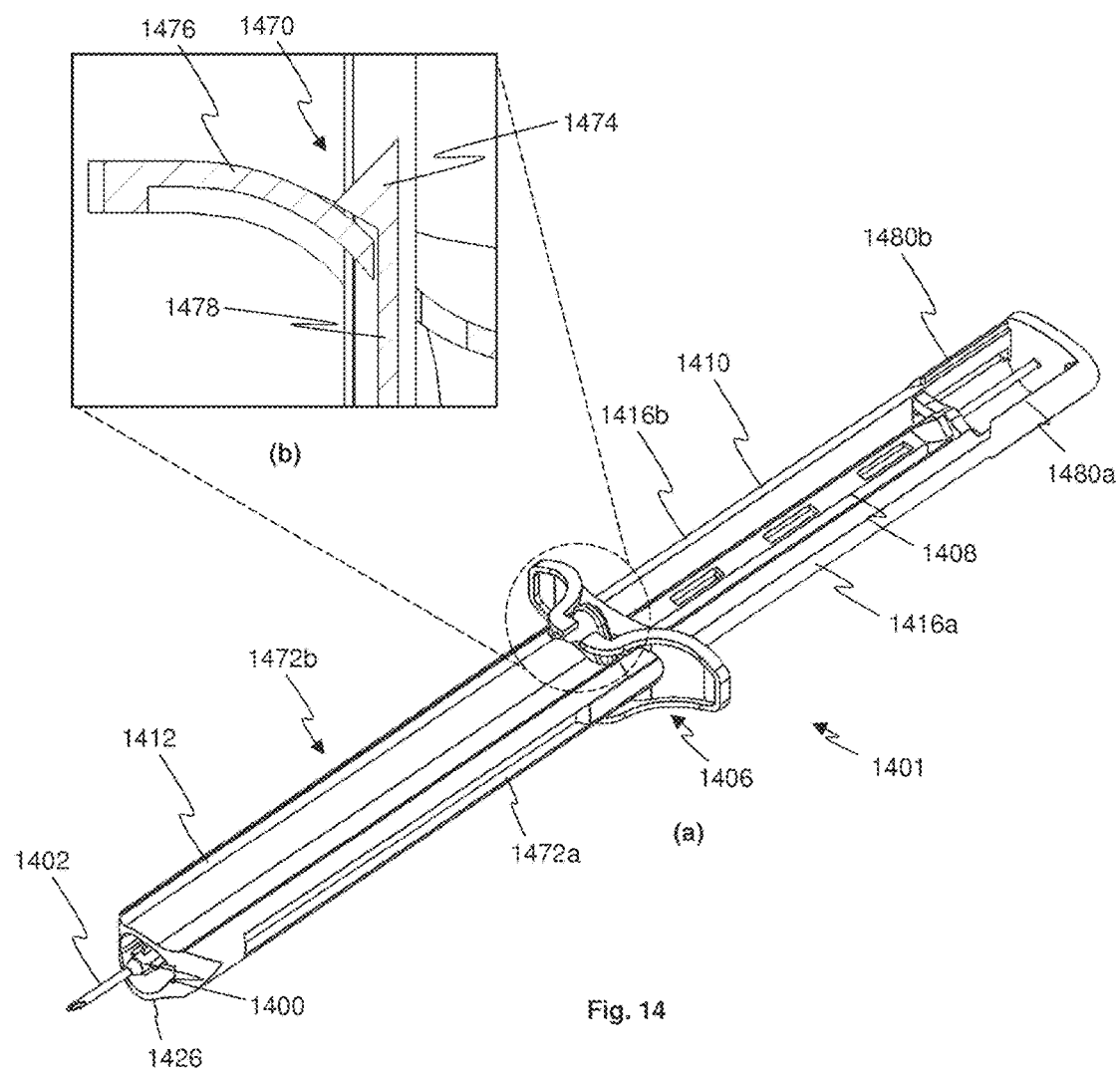
Figure 15:
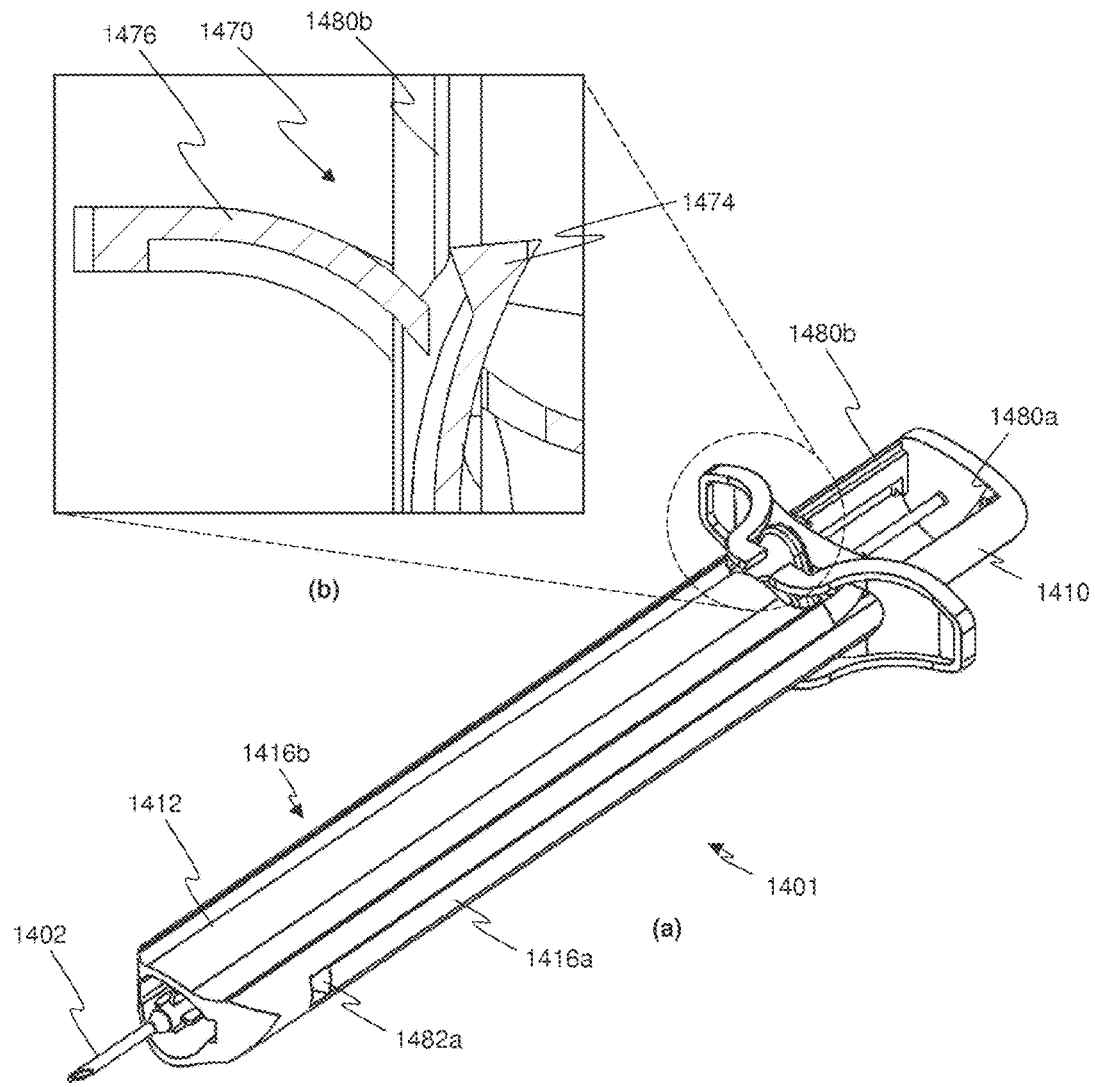
Figure 16:
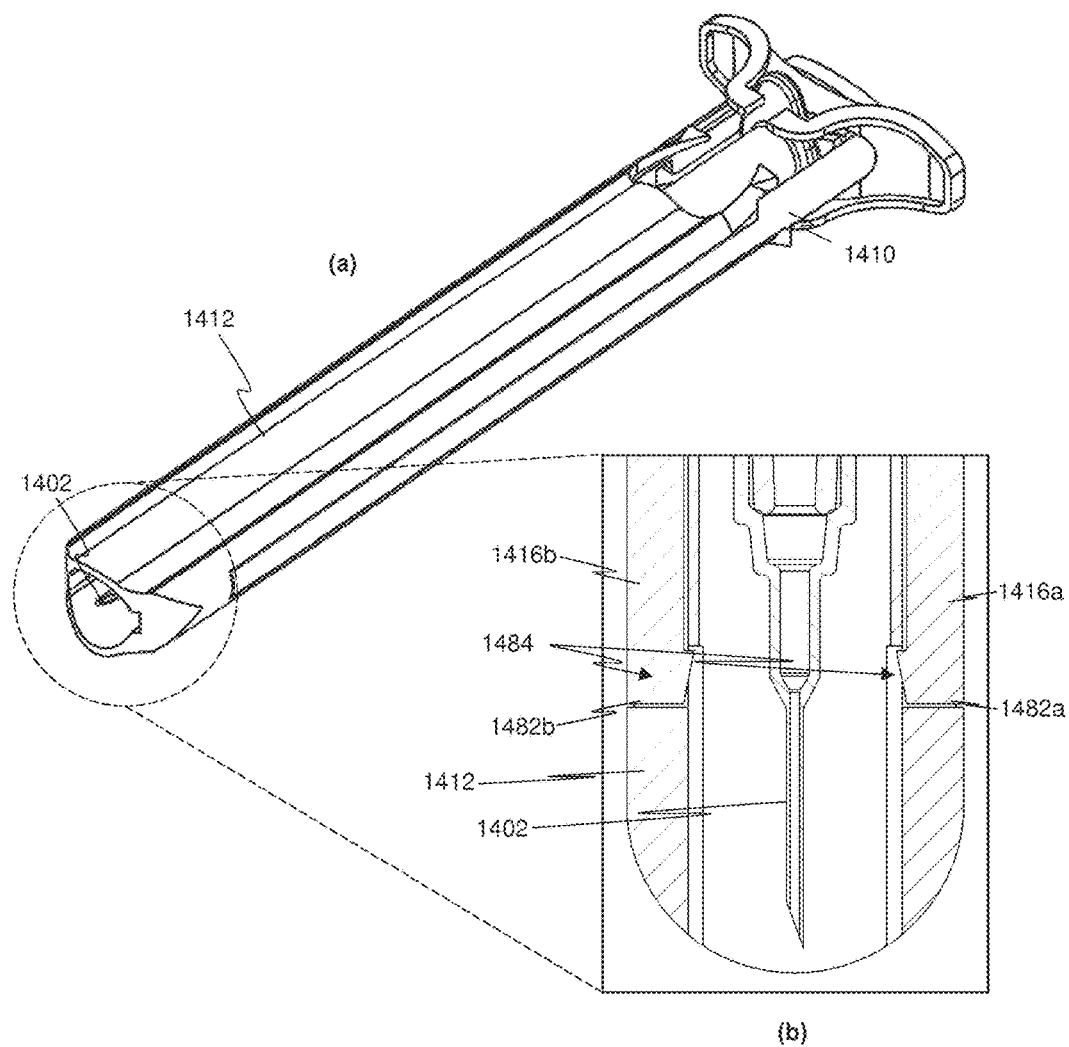
FIG. 16a is an isometric view of a safety syringe with a plunger in a third position along its inward stroke.
FIG. 16b is a section through a sheath locking means in a locked position.

In the exemplary apparatus of FIG. 1, the safety plunger 110 is coupled to the sheath 112 and comprises a head 114 and arms 116a, 116b connecting the head 114 to the sheath 112. The arms 116a, 116b are moveable along the outside of the barrel 104 such that the sheath 112 moves along the outside of the barrel 104 on application of a force to the head 114. In exemplary safety syringes and safety syringe apparatus, the safety plunger 110 may be manufactured as a plurality of separate features that can be assembled later. For example, the sheath 112 may be manufactured as one piece and the arms 116a, 116b and head 114 may be manufactured as one piece. During assembly, the two pieces may be joined together by some connection means, such as an interference or snap fit arrangement. Manufacturing the safety plunger 110 in a plurality of pieces means that overall assembly of the safety syringe is made easier, as the safety plunger 110 may be assembled around the syringe plunger 108 rather than having to guide the syringe plunger 108 into the safety plunger 110. In addition, the safety plunger and the sheath may be separate units capable of independent movement during at least part of the inward stroke of the safety syringe. An example of such an arrangement is shown in FIGS. 14 to 16 and described in detail below.

The needle 102 may be any type suitable for the task to be undertaken by the user, such as injecting a drug into a patient or taking a fluid from a patient. In exemplary safety syringes 100, the needle 102 is fixedly attached to the open end of the barrel 104. In other exemplary safety syringes 100, the needle 102 may be removably attached to the barrel 104. In such safety syringes 100, the needle 102 may be replaced by other needles of the same or a different type.

The barrel 104 is tapered at the open end towards the point at which the needle 102 is connected. In the exemplary safety syringe 100 of FIG. 1, the barrel 104 comprises a tapered internal surface 118. As will be explained later, the tapered internal surface may receive and thereby compress a resiliently deformable plunger tip fitted to the syringe plunger 108. The barrel 104 may be prefilled with a substance, for example a medicament, such that the safety syringe 100 is ready to use from the packet.

The handle portion 106 comprises a main body 120 and flanges 122a, 122b extending laterally from the main body 120. The main body 120 comprises a portion that surrounds the barrel 104 and is fixed thereto. The flanges 122a, 122b are configured to receive the index finger and middle finger of a user while the thumb applies a force to the head 114 of the safety plunger 110, although any combination of fingers and/or thumb could be used. The handle portion 106 is fixed to the barrel 104 by an aperture 124 configured to receive a radially protruding lip of an opening of the barrel at a distal end to the opening coupled to the needle 102. The lip may be received by way of a snap fit to hold it in the aperture 124.

The sheath 112 may be at least partially received within the main body 120 of the handle portion 106 when the syringe plunger 108 is at the outermost part of its stroke.

The arms 116a, 116b of the safety plunger 110 are configured to pass through the handle portion 106 such that the safety plunger 110 may move in its stroke relative to the handle portion 106 and, therefore, the barrel 104. The sheath 112 is configured to travel along the outside of the barrel 104 with the inward stroke of the safety plunger 110 until the sheath 112 at least partially covers the needle 102. At the innermost point of the stroke of the safety plunger 110, the end 126 of the sheath 112 is beyond the end of the needle 102, such that the sharp point of the needle 102 is not exposed.

The arms 116a, 116b comprise coupling recesses 128a, 128b (only coupling recess 128b can be seen in FIG. 1). The syringe plunger 108 comprises lugs 130a, 130b (only lug 130b can be seen in FIG. 1) configured to be received in coupling recesses 128a, 128b. The lugs are on a head 132 of the syringe plunger 108, which is located at an outer end of the syringe plunger 108. The lugs 130a, 130b and coupling recesses 128a, 128b are configured such that rotation of the syringe plunger 108 may engage and disengage the lugs 130a, 130b within the coupling recesses 128a, 128b. When the lugs 130a, 130b are engaged in the coupling recesses 128a, 128b, the safety plunger 110 is coupled to the syringe plunger 108. When the lugs 130a, 130b are disengaged from the coupling recesses 128a, 128b, the safety plunger 110 is decoupled from the syringe plunger 108.

The syringe plunger 108 comprises a rotation surface 134. The rotation surface is configured to interact with a reaction surface (not shown in FIG. 1) to rotate the syringe plunger 108. The rotation surface may be a ramped or angled portion of the syringe plunger 108. The reaction surface is fixed with respect to the barrel 104. In the exemplary embodiment of FIG. 1, the syringe plunger 108 has a cross-shaped section along its body. The handle portion 106 comprises a cross-shaped aperture corresponding to the cross-shape of the syringe plunger 108. As the syringe plunger 108 passes along its stroke, the cross-shaped body of the syringe plunger 108 passes through the cross shaped aperture of the handle portion 106. The rotation surface 134 comprises an angled portion of the cross-shape of the body of the syringe plunger 108. Each extension of the cross-shaped body is so angled. The effect is that when the rotation surface 134 reaches the cross-shaped aperture in the handle portion 106, the syringe plunger 108 is rotated. Other methods of rotating the syringe plunger 108 are possible and some are discussed herein.

The stroke of the safety plunger 110 is greater in length than the stroke of the syringe plunger 108, as the arms 116a, 116b extend beyond the head 132 of the syringe plunger 108. Therefore, a gap 136 exists between the head 114 of the safety plunger and the head 132 of the syringe plunger. As explained below, a guard may be positioned to prevent a user inserting a finger or thumb into the gap 136 and applying a force directly to the head 132 of the syringe plunger 108.

FIGS. 2a-6a show isometric views of a safety syringe 100 at various positions along the inward stroke of the safety plunger 110 (and therefore the syringe plunger 108 by way of the coupling of the two). The operation of the safety syringe 100 will be described below with reference to FIGS. 2a-6a.

FIG. 2a shows the safety syringe 100 with both the syringe plunger 108 and the safety plunger 110 fully extended and at the outermost points of their strokes. The syringe plunger 108 is coupled to the safety plunger 110, as the lugs 130a, 130b of the head 132 of the syringe plunger 108 are engaged in the coupling recesses 128a, 128b in the arms 116a, 116b of the safety plunger. In this way, the syringe plunger 108 is coupled to the sheath 112, which forms part of the safety plunger 110. The barrel 104 may be prefilled with a substance, such as a medicament.

A user may place the index finger and middle finger of one hand against the flanges 122a, 122b of the handle portion 106 and the thumb of the same hand on the head 114 of the safety plunger 110. The user then applies a relative force to the head 114 and the handle portion 106 by closing the thumb towards the index and middle fingers. For the sake of clarity, this relative force will be considered herein as a force on the head 114.

The force applied to the head 114 begins the inward stroke of the safety plunger 110. As the safety plunger 110 and the syringe plunger 108 are coupled, the inward stroke of the syringe plunger 108 also begins. The safety plunger 110 and the syringe plunger 108 move together.

FIG. 3a shows the safety syringe 100 part way through the inward strokes of both the syringe plunger 108 and the safety plunger 110. The syringe plunger 108 and the safety plunger 110 have moved together under the force applied to the head 114 to a point at which the rotation surface 134 is about to interact with the reaction surface on the handle portion 106.

Continued application of the force on the head 114 leads the syringe plunger 108 to decouple from the safety plunger, as shown in FIG. 4a. To show this more clearly, part of the safety syringe 100 has been cut away in FIG. 4a. The rotation surface 134 that is angled with respect to the direction of travel of the syringe plunger 108 has interacted with the reaction surface and the syringe plunger 108 has been rotated. As a result, the lugs 130a, 130b (only lug 130b is visible in FIG. 4a) on the head 132 of the syringe plunger 108 have become disengaged from the coupling recesses 128a, 128b in the arms 116a, 116b. The safety plunger 110 is now free to move relative to the syringe plunger 108. That is, the safety plunger 110 is free to move while the syringe plunger 108 remains stationary. As set out above, the force applied by the user to begin the strokes of the safety plunger 110 and the syringe plunger 108 is used to decouple the two. Continued application of force to the head 114 will continue the inward stroke of the safety plunger 110.

The point at which the decoupling occurs may be the point at which the syringe plunger 108 has completed its inward stroke. That is, the decoupling may occur at the innermost point of the stroke of the syringe plunger 108. This ensures that all of the substance contained within the barrel 104 has been expelled from the syringe 100 before decoupling. It is noted once again that, in the exemplary apparatus of FIGS. 1 to 6, decoupling of the safety plunger 110 from the syringe plunger 108 leads to decoupling of the sheath 112 from the syringe plunger 108, as the sheath forms part of the safety plunger 108.

FIG. 5a shows the continued travel of the safety plunger 110 with continued application of a force to the head 114. The safety plunger 110 continues to pass through the handle portion 106 and continues to extend further down the length of the syringe 100. The sheath 112 has now extended beyond the end of the barrel 104 and now partially covers the needle 102.

As shown in FIG. 6a, when the inward stroke of the safety plunger 110 has been completed, the head 114 abuts the handle portion 106 and also abuts the head 132 of the syringe plunger 108. In this position the sheath 112 has extended such that it completely surrounds the needle 102. The end 126 of the sheath 112 extends beyond the tip of the needle 102 such that the needle is not exposed. In this position, the safety syringe 110 may lock in relation to the barrel 104 and needle 102, such that the needle 102 cannot become exposed. In exemplary safety syringes, the safety plunger 110 may become locked to the handle portion 106.

FIGS. 2b-6b show the operation of a locking mechanism for locking the safety plunger 110 in a position in which the sheath 112 is covering the needle 102. The locking mechanism locks the safety plunger 110 in relation to the barrel 104 at the innermost point of the stroke of the safety plunger 110. Herein, the locking mechanism shown in FIGS. 2b-6b may be termed a biased locking mechanism to help differentiate it from other locking mechanisms, such as the snap fit locking mechanism shown in FIG. 17. As explained below, the biased locking mechanism may be biased by a resiliently deformable tip of the syringe plunger, or by an alternative outwardly biasing member.

Referring to FIG. 2b, one of the lugs 130a, 130b (from here on referred to as 130 when describing the locking mechanism) is shown in a channel 138. The channel is formed in one of the arms 116a, 116b of the safety plunger. For the avoidance of doubt, it is noted that in exemplary embodiments, channels 138 may be formed in both arms 116a, 116b.

In embodiments in which there is no locking mechanism or a different locking mechanism to that shown in FIGS. 2b-6b, only the coupling recess 128a, 128b (from here on referred to as 128 when describing the locking mechanism) may be formed in the arms 116a, 116b. For illustrative purposes, the coupling recess 128 is shown in hatched shading in FIGS. 2b-6b.

The channel 138 is substantially C-shaped. In exemplary locking mechanisms, the channel 138 is a skewed C-shape. The channel comprises the coupling recess 128, a substantially longitudinal portion 140 and a return recess 142. The lateral extent of the return recess 142 is less than the lateral extent of the coupling recess 128.

In FIG. 2b, the lug 130 is positioned in the coupling recess 128 and so the safety plunger 110 and the syringe plunger 108 are coupled. The lateral position of the lug 130 is that before twisting and is defined by the cross-shaped main body of the syringe plunger 108 and the corresponding cross-shaped aperture in the handle portion. It is noted that the lateral position of the lug 130 may be defined by other means.

In FIG. 3b, the safety plunger 110 has made part of its inward stroke and has reached a point just before decoupling from the syringe plunger 108. The lug 130 is still positioned in the coupling recess 128.

In FIG. 4b, the inward stroke of the safety plunger 110 and the syringe plunger 108 have reached the point at which the syringe plunger 108 has rotated. At this point, the lug 130 has disengaged from the coupling recess 128 and the safety plunger 110 and syringe plunger are decoupled. This is shown in FIG. 4b by the lug 130 having exited the coupling recess and entered the substantially longitudinal channel 140. Further inward motion of the safety plunger 110 will be independent of the syringe plunger 108.

In FIG. 5*b*, the safety plunger 110 has travelled further along its inward stroke independently of the syringe plunger 108, which has remained stationary. Therefore, the lug 130 has travelled down the substantially longitudinal channel 140.

The syringe plunger comprises a resiliently deformable tip, which may be compressed at the end of the barrel 104 before the needle 102. Such compression results in a biasing force urging the syringe plunger 108 back up the barrel 104 to begin its outward stroke. As the lug 130 meets and is pushed against the end of the substantially longitudinal channel 140, continued force applied to the head 114 of the safety plunger 110 also applies a force to the syringe plunger 108 and compresses the resiliently deformable tip of the syringe plunger 108. In this way, the syringe plunger 108 and the safety plunger 110 are temporarily recoupled to compress the resiliently deformable tip.

As the force is removed from the head 114 of the safety plunger, the biasing force resulting from the compression of the resiliently deformable tip begins to move the syringe plunger outward to begin its outward stroke. With outward movement of the syringe plunger 108, the rotation surface 134 is configured to interact again with the or another reaction surface that is fixed in relation to the barrel 104 and the syringe plunger begins to rotate back such that the lug 130 enters the return recess 142. This is shown in FIG. 6*b*. The lug 130 meets the lateral extent of the return recess 142 before the syringe plunger 108 as rotated back fully, as the lateral extent of the return recess 142 is less than the lateral extent of the coupling recess 128.

As the lug 130 enters the return recess 142, it is prevented from travelling up the substantially longitudinal channel 140 and the safety plunger 110 is locked to the syringe plunger 108. Any attempt the separate the safety plunger 110 and syringe plunger 108 urges the lug 130 further into the return recess, reinforcing the lock.

Further, the syringe plunger 108 is locked with respect to the barrel 104 and cannot travel on its outward stroke. This is because the lug 130 reaches the lateral extent of the return recess 142 before the syringe plunger 108 has fully rotated back and so the rotation surface 134 has not fully passed the reaction surface. The only way that the syringe plunger 108 can continue its outward stroke is if it continues to rotate, but this is prevented by the lug 130 reaching the end of the return channel 142. Therefore, the syringe plunger 108 is locked in the barrel 104 and, as it is locked to the syringe plunger 108, the safety plunger 110 is also locked with respect to the barrel 104. This keeps the sheath 112 in place covering the needle 102.

As set out above, the full inward stroke of the safety plunger fulfils two actions: the dispensing of the substance in the barrel 104 and the covering of the needle 102 by the sheath 112. These two actions are completed with only a single action from the user. Moreover, the single action for the user is entirely intuitive, as it is no different from the action required to use a standard syringe, that of depressing a plunger. The only difference is that the inward stroke is slightly longer. Further, healthcare professionals are trained always to complete the inward stroke when using syringes. Therefore, when acting out that training, a healthcare professional using the safety syringe 100 would also engage the sheath 112 over the needle 102. As such, the safety syringe 100 has improved safety.

Also, the action of completing the inward stroke of the safety plunger 110 after decoupling from the syringe plunger 108 pushes the end surface 126 of the sheath 112 against the skin of the patient and extracts the needle 102 therefrom. This is done under a normal amount of force applied by a user that is steadily applied rather than the high force rapidly applied by a spring in known safety syringes. Therefore, discomfort and bruising for the patient is reduced.

In exemplary safety syringes, the safety plunger 110 is free to move through the handle portion 106 with little or no resistance. In contrast, the movement of the syringe plunger 108 in the barrel 104 offers an amount of resistance. As a result, after decoupling of the syringe plunger 108 from the safety plunger 110, there is a sharp drop off in resistance and therefore the force required to move the safety plunger 110 is lower when decoupled. This means that it is very difficult for a user to stop the inward stroke before the sheath 112 has extended beyond the tip of the needle, as it happens rapidly. In other safety syringes, movement of the safety plunger 110 through the handle portion may be damped to offer some resistance.

In the above exemplary safety syringe 100, rotation of the syringe plunger 108 is used to decouple it from the safety plunger 110. However, there are many other ways in which this may be implemented and these are covered within the scope of the appended claims. Mechanisms for implementing the decoupling may include one or more of the following:

A rotational engagement, where the plunger is driven by a horizontal slot or coupling recess in the safety plunger;

A clip engagement, where biased clips retain the plunger until they are displaced by displacement surfaces fixed in relation to the barrel;

A frangible engagement, wherein the syringe plunger and safety plunger are moulded as one component and the small plastic "bridge" that connects them is severed;

A magnetic engagement, in which magnets in the safety plunger attract a metallic element in the syringe plunger (or vice versa);

A string/rope/thread engagement, where the syringe plunger is pulled by "tethers" on the safety plunger which are de-latched or broken;

An interference engagement, in which the syringe plunger is "wedged" into a bottle neck in the safety plunger and driven forwards by friction;

An adhesive engagement, where a glue is used to couple the syringe plunger and the safety plunger;

A suction engagement, whereby the syringe plunger is coupled to the safety plunger by air Electronics—electromagnetism, smart materials, computer controlled latches may also be used;

A gear engagement; and

A ratchet engagement.

Figure 8:
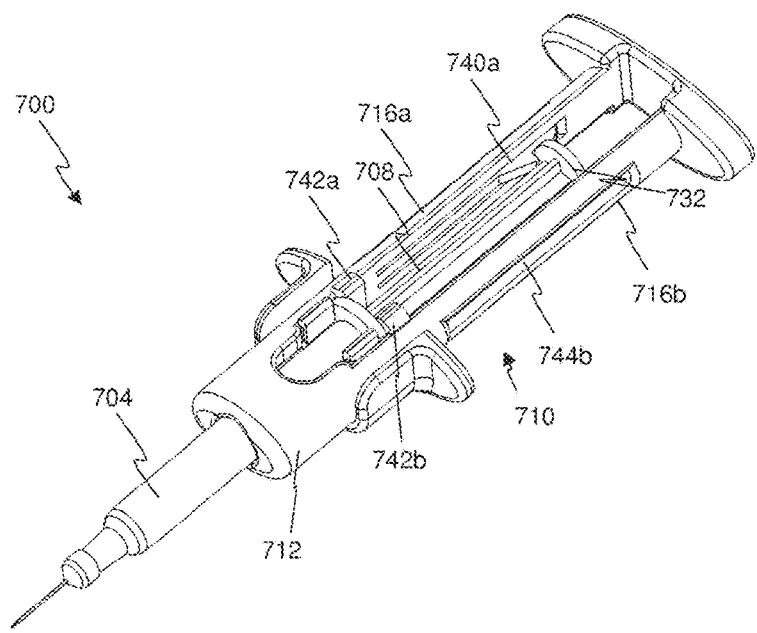
FIG. 8 is an isometric view of a safety syringe.

FIGS. 7 and 8 show a side elevation and isometric view of a safety syringe 700 respectively. In FIG. 7, the syringe plunger 708 and the safety plunger 710 are coupled by bias clips 740*a*, 740*b* arranged on the internal faces of the arms 716*a*, 716*b* of the safety plunger 710. The clips 740*a*, 740*b* are biased towards a central axis of the safety syringe 700 and are configured to retain the head 732 of the syringe plunger 708, such that the syringe plunger 708 and the safety plunger 710 are coupled and, thereby, the syringe plunger 708 and the sheath 712 are coupled.

Displacement surfaces 742*a*, 742*b* that are fixed in relation to the barrel 704 are configured to displace the biased clips 740*a*, 740*b* as they pass the displacement surfaces 742*a*, 742*b*. The displacement is away from the central axis of the safety syringe 700 and therefore has the effect of releasing the head 732 of the syringe plunger 708. This, in turn, decouples the syringe plunger 708 from the safety plunger 710. As can be seen in FIG. 8, the arms 716a, 716b may comprise slots or recesses 744a, 744b into which the clips 740a, 740b may move when they are displaced.

In aspects other than the coupling/decoupling arrangement of the syringe plunger 708 and the syringe plunger 710, the safety syringe 700 may comprise one or more features of the safety syringe 100.

Figure 9:
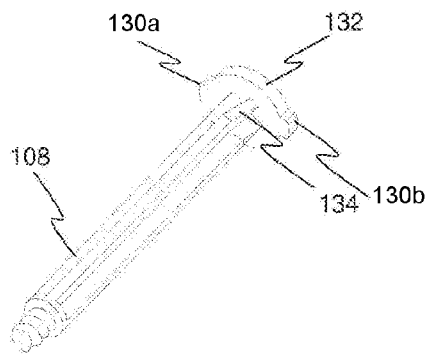
FIG. 9 is an isometric view of a plunger.

FIG. 9 shows the syringe plunger 108 of FIG. 1 in isolation.

Figure 10:
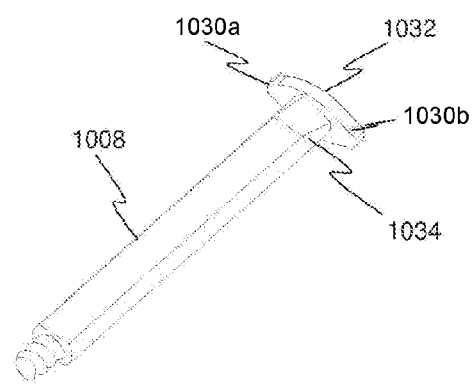
FIG. 10 is an isometric view of a plunger.

FIG. 10 shows an alternative syringe plunger 1008 that may be used when decoupling of the syringe plunger from the safety plunger is by rotation of the syringe plunger. The syringe plunger 1008 may, for example, be used in the safety syringe 100 of FIG. 1. As can be seen in FIG. 10, the main body of the syringe plunger 1008 has a substantially rectangular cross section. A top portion of the syringe plunger 1008 is twisted with respect to the main body such that a rotation surface 1034 is provided. In exemplary safety syringes, the syringe plunger 1008 may pass through an aperture in the handle portion that corresponds to the cross section of the main body of the syringe plunger 1008. As the rotation surface 1034 reaches the aperture, the syringe plunger 1008 is caused to rotate as the top portion is twisted. The syringe plunger 1008 also comprises a head 1032 and lugs 1030a, 1030b thereon, which operate in a similar way to those described above.

Figure 10A:
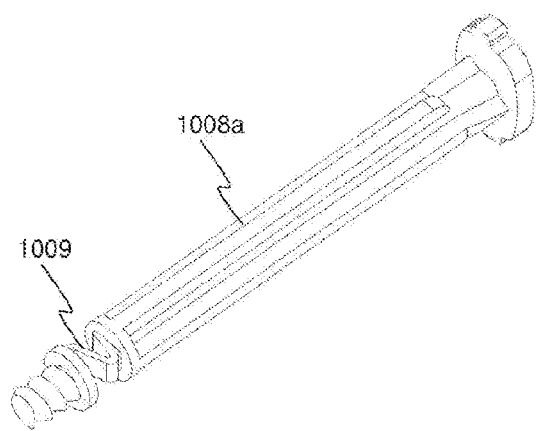
FIG. 10a is an isometric view of a plunger.

FIG. 10a shows an exemplary syringe plunger 1008a comprising a lost motion device 1009. The lost motion device 1009 is configured to compress, if needed, at the end of the barrel of a syringe to account for tolerances in the manufacture of the barrel. Tolerances in barrel manufacture can be relatively high when compared with tolerances for other features of a safety syringe. As a result of this, a syringe plunger may reach the end of its inward stroke when the tip of the syringe plunger has not reached the end of the barrel, leaving some of the substance in the barrel. In the case of drug delivery, this is to be avoided. Conversely, the tip of the syringe plunger may reach the end of the barrel before the decoupling means has decoupled the syringe plunger from the safety plunger, preventing the location of the sheath around the needle.

Therefore, the syringe plunger may be manufactured to be slightly longer than the barrel and a lost motion device 1009 positioned along its length. The lost motion device is a compressible element in the syringe plunger 1008a that compresses if the tip of the syringe plunger 1008a reaches the end of the barrel before the end of the inward stroke of the syringe plunger 1008a. This ensures that the tip of the syringe plunger 1008a always reaches the end of the barrel and that the decoupling means always activates.

The lost motion device 1009 may be a spring, as in FIG. 10a, but may also be any other compressible device or material, such as foam or an elastomeric material.

Figure 11:
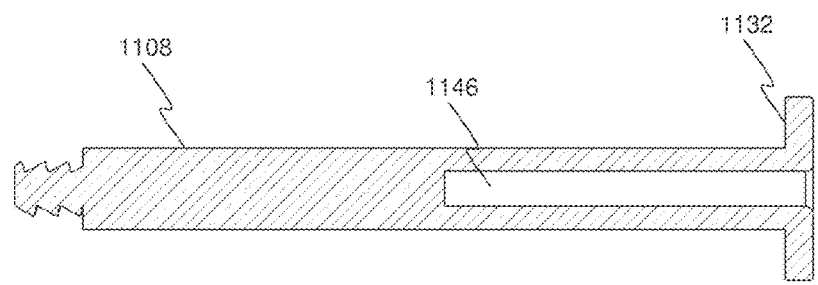
FIG. 11 is a section through a plunger.

FIG. 11 shows a syringe plunger 1108 comprising a central bore 1146 in the head 1132 that extends along the length of the syringe plunger 1108. The central bore 1146 may be incorporated into any of the syringe plungers covered within the scope of this document. The central bore 1146 may be configured to receive a guard (mentioned above) that sits in the gap 136 shown in FIG. 1. The guard may be a pin or rod attached to the underside of the head 132 and aligned with the central bore 1146. The guard is configured to prevent a user inserting their thumb or finger into the gap 136 and applying a force directly to the head 132 of the syringe plunger 108, as to do so could result in use of the safety syringe 100 without deployment of the sheath 112.

Figure 12:
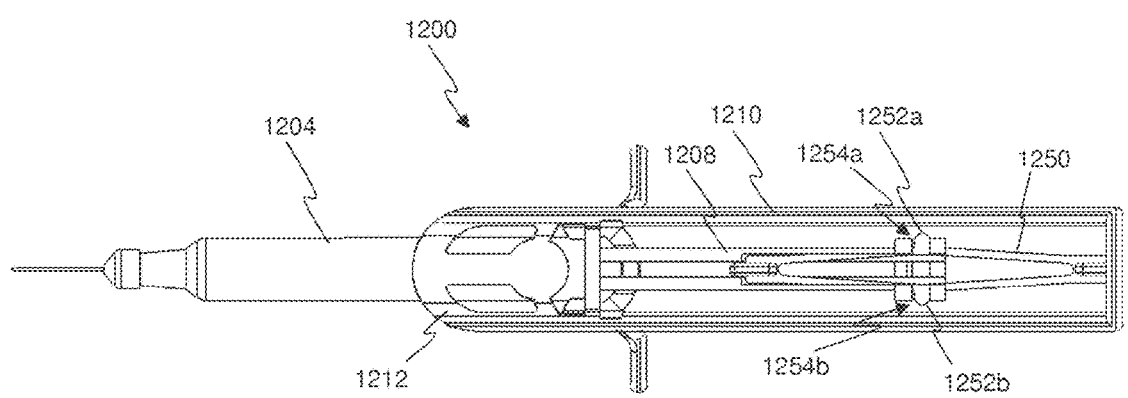
FIG. 12 is a side elevation of a safety syringe.

FIG. 12 shows an exemplary safety syringe 1200. The safety syringe 1200 comprises a decoupling mechanism that does not require a handle portion in order to operate. More specifically, the safety syringe 1200 comprises a decoupling mechanism able to operate with only features of the safety plunger 1210 and the syringe plunger 1208. Such a decoupling mechanism may be provided in many ways and the safety syringe 1200 is one example.

The safety plunger 1210 comprises a laterally outwardly biased member 1250. The biased member 1250 comprises two retaining lugs 1252a, 1252b biased laterally outwardly and configured to engage with corresponding retaining means (e.g., recesses or apertures 1254a, 1254b) in the syringe plunger 1208. As the syringe plunger 108 enters a barrel 1204 of the safety syringe, the internal walls of the barrel 1204 travel up the outside of the syringe plunger 1208 until they interact with the retaining lugs 1252a, 1252b pushing them laterally inwards and overcoming the bias imparted by the biasing member 1250. Continued longitudinally inward force applied to the safety plunger 1210 forces the retaining lugs 1252a, 1252b over the corresponding retaining means of the syringe plunger 1208 and decouples the safety plunger 1210 and the syringe plunger 1208.

Figure 13:
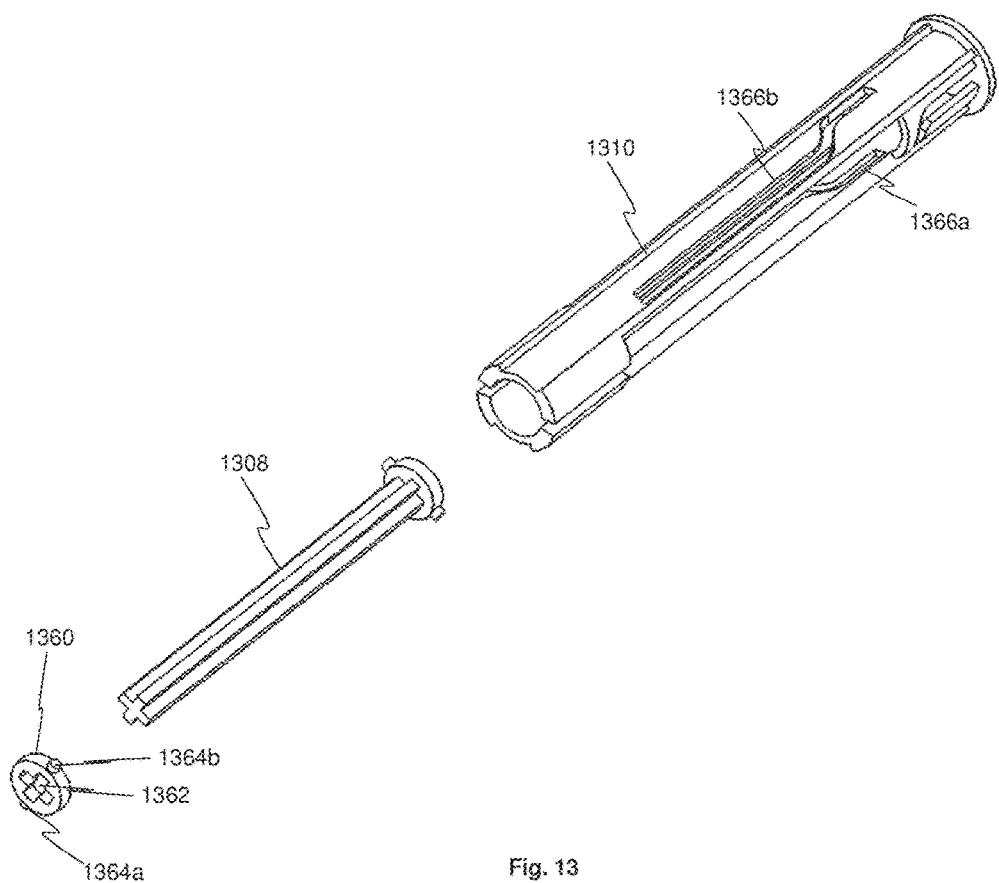
FIG. 13 is an exploded isometric view of a syringe plunger and safety plunger.
Figure 13A:
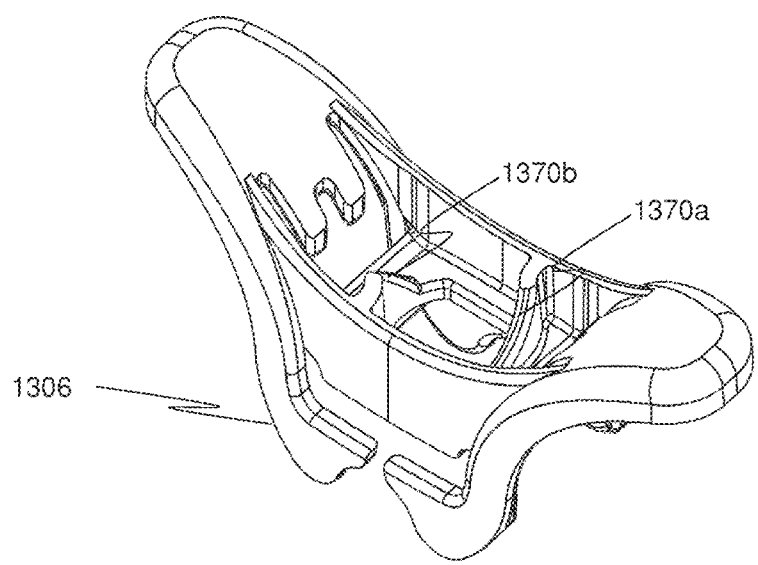
FIGS. 13a and 13b show isometric views of a handle portion and a syringe plunger.
Figure 13B:
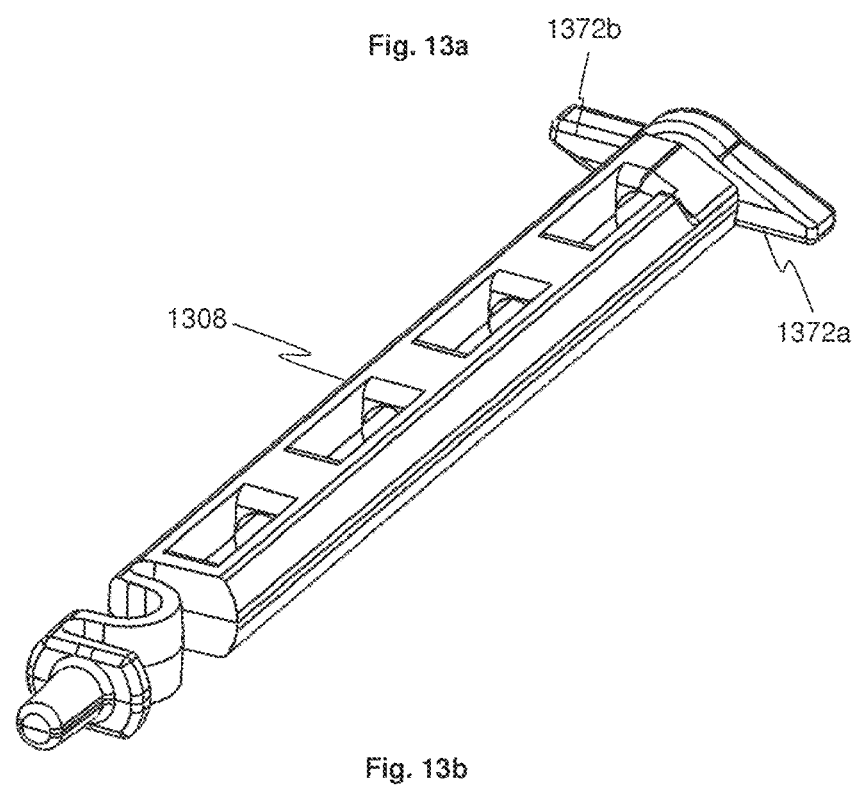

FIG. 13 shows an exemplary safety plunger 1310 and syringe plunger 1308. Together, the safety plunger 1310, syringe plunger 1308 and a barrel end cap 1360 are configured to rotate the syringe plunger 1308 at a point on the inward stroke thereof. It is noted that there is no rotation surface on the syringe plunger 1308. The syringe plunger 1308 may be a standard syringe plunger provided with a syringe and need not be specifically designed. It is also noted that there are many ways that rotation of the syringe plunger 1308 relative to the safety plunger 1310 may be achieved and the exemplary arrangement in FIG. 13 shows one way. In a specific safety syringe apparatus, one or more rotation surfaces may be located on the handle portion (e.g. on the finger flange) rather than on a separate component, as in FIG. 13. For example, in FIGS. 13a and 13b rotation surfaces 1370a, 1370b are located on the handle portion 1306. The rotation surfaces 1370a, 1370b comprise angled surfaces configured to interact with protrusions 1372a, 1372b on the syringe plunger 1308 to rotate the syringe plunger 1308 as the protrusions 1372a, 1372b pass over the rotation surfaces 1370a, 1370b on the inward stroke of the syringe plunger 1308.

The barrel end cap 1360 comprises a cross-shaped aperture 1362 configured to receive the cross-shaped cross section of the syringe plunger 1308. Rotation of the syringe plunger 1308 is provided through rotation of the barrel end cap 1360. For this purpose, the barrel end cap comprises rotation lugs 1364a, 1364b configured to travel within rotation channels 1366a, 1366b in the safety plunger 1310. As the safety plunger 1310 travels on its inward stroke, the rotation lugs 1364a, 1364b travel through the rotation channels 1366a, 1366b, which comprise angle sections that rotate the barrel end cap 1360 with inward movement of the safety plunger 1310. Rotation of the barrel end cap 1360 rotates the syringe plunger 1308 and thereby decouples the syringe plunger 1308 from the safety plunger 1310, as discussed above.

FIGS. 14 to 16 show a syringe 1400 fitted with an exemplary safety syringe apparatus 1401. As above, the syringe 1400 and the safety syringe apparatus 1401 may together form a safety syringe. The safety syringe apparatus 1401 comprises a safety plunger 1410 and a sheath 1412. Many of the features of the syringe 1400 and the safety syringe apparatus 1401 are similar to those described above in respect of any of the other exemplary apparatus. As such, a description of those features is not given again here and corresponding reference numerals are used to identify them in FIGS. 14 to 16.

Referring to FIG. 14*a*, the safety syringe apparatus 1401 is shown in an extended state. That is, the safety plunger 1410 and the syringe plunger 1408 are at the outermost point of their inward strokes. The safety plunger 1410 is coupled to the syringe plunger 1408 by way of lugs and corresponding coupling recesses.

The sheath 1412 is initially decoupled from the safety plunger 1410 and is configured to couple to the safety plunger 1410 at a point on the inward stroke of the safety plunger 1410. After coupling of the sheath 1412 and the safety plunger 1410, further inward movement of the safety plunger 1410 results in movement of the sheath 1412 towards and over the end of the barrel of the syringe 1400 and the hypodermic needle 1402.

Initially, the sheath 1412 is fixed with respect to the syringe 1400 by a sheath retaining means 1470, which is shown in greater detail in FIG. 14*b* and described below.

An end 1426 of the sheath 1412 is substantially level with a point on the syringe 1400 at which the hypodermic needle 1402 begins, or a small distance, e.g. 1-5 mm back from that point. All of the hypodermic needle is exposed when the safety syringe apparatus 1401 is in its extended state.

In the exemplary safety syringe apparatus 1401 of FIGS. 14 to 16, the sheath 1412 comprises channels 1472*a*, 1472*b* (not shown). The channels 1472*a*, 1472*b* correspond to arms 1416*a*, 1416*b* of the safety plunger 1410 and are configured to allow travel of one of the arms 1416*a*, 1416*b* within each channel 1472*a*, 1472*b* during the inward stroke of the safety plunger 1410.

As shown in FIG. 14*b*, the exemplary sheath retaining means 1470 comprises a sheath latch 1474. The sheath latch 1474 is engaged with a sheath retaining lip 1476. In exemplary safety syringe apparatus, the sheath retaining lip 1476 may be part of a handle portion 1406 that is fixed with respect to the syringe 1400. Therefore, when the sheath latch 1474 is engaged with the sheath retaining lip 1476, the sheath is fixed in relation to the syringe 1400. The top surface of the sheath 1412 abuts the underside of the handle portion 1406, or could be modified to meet the underside of the syringe flange 1400. The sheath latch 1474 is held in position engaged with the sheath retaining lip 1476 by a biasing force, in this case provided by a resiliently deformable sheath arm 1478 on which the sheath latch 1474 is located. There may be a plurality of sheath retaining means. For example, on opposed sides of the sheath 1412 (and handle portion 1406).

FIG. 15*a* shows the safety syringe apparatus 1401 at a point on the inward stroke of the safety plunger 1410 at which the safety plunger 1410 decouples from the syringe plunger 1408, as described above in relation to other apparatus. In addition, the sheath retaining means 1470 is released, such that the sheath 1412 is no longer fixed in relation to the syringe 1400, which may occur at the same point in the inward stroke of the safety plunger 1410 as the point at which the safety plunger 1410 decouples from the syringe plunger 1408.

The safety plunger 1410 is configured to release the sheath retaining means 1470 such that the sheath 1412 is able to move independently of the syringe 1400. For this purpose, the safety plunger 1410 comprises sheath releasing flanges 1480*a*, 1480*b* that are configured to interact with the sheath latch 1474 to release the sheath retaining means 1470. Specifically, the sheath releasing flanges 1480*a*, 1480*b* comprise angled surfaces that contact the sheath latch 1474 as the safety plunger 1410 travels on the inward stroke to overcome the biasing force holding the sheath latch 1474 in engagement with the sheath retaining lip 1476.

As can be seen in FIG. 15*a*, the arms 1416*a*, 1416*b* have been received in the channels 1472*a*, 1472*b* of the sheath 1412. End faces 1482*a*, 1482*b* of the arms 1416*a*, 1416*b* is shown in FIG. 15*a* to be just short of the ends of the channels 1472*a*, 1472*b*. Continued movement of the safety plunger 1410 on its inward stroke results in contact between the end faces 1482*a*, 1482*b* with the ends of the channels 1472*a*, 1472*b* to couple the safety plunger 1410 with the sheath 1412. Continued movement of the safety plunger 1410 after coupling with the sheath 1412 results in movement of the sheath 1412 down the barrel of the syringe 1400 and over the hypodermic needle 1402.

It is noted that the safety plunger 1410 couples to the sheath 1412 at a first point (location) on the inward stroke of the safety plunger 1410 and decouples from the syringe plunger 1408 at a second point (location) on the inward stroke of the safety plunger 1410. In addition, the safety plunger 1410 is configured to release the sheath retaining means at a third point (location) on its inward stroke. However, the terms "first", "second" and "third", when used in this context need not indicate an order in which the two points are reached on the inward stroke. In particular, in exemplary safety syringe apparatus, the first point may be before the second point, the first point may be the same as the second point or the first point may be after the second point.

FIG. 16*a* shows the safety syringe apparatus 1401 after use when the safety plunger 1410 has completed its inward stroke. The sheath 1412 is extended beyond the end of the barrel of the syringe 1400 to cover the hypodermic needle 1402.

As shown in FIG. 16*b*, the arms 1416*a*, 1416*b* of the safety plunger 1410 have extended into the channels 1472*a*, 1472*b* of the sheath 1412 such that the end faces 1482*a*, 1482*b* of the arms 1416*a*, 1416*b* connect with the ends of the channels 1472*a*, 1472*b*. In addition, a coupling locking means 1484 locks the sheath 1412 and the safety plunger 1410 in a coupled state. In the exemplary safety syringe apparatus 1401 of FIG. 16*b*, the coupling locking means 1484 comprises a latch on the arms 1416*a*, 1416*b* that engages with a lip in the channels 1472*a*, 1472*b*. Engagement is provided by a biasing force applied by a resilience of the arms 1416*a*, 1416*b*.

Figure 17:
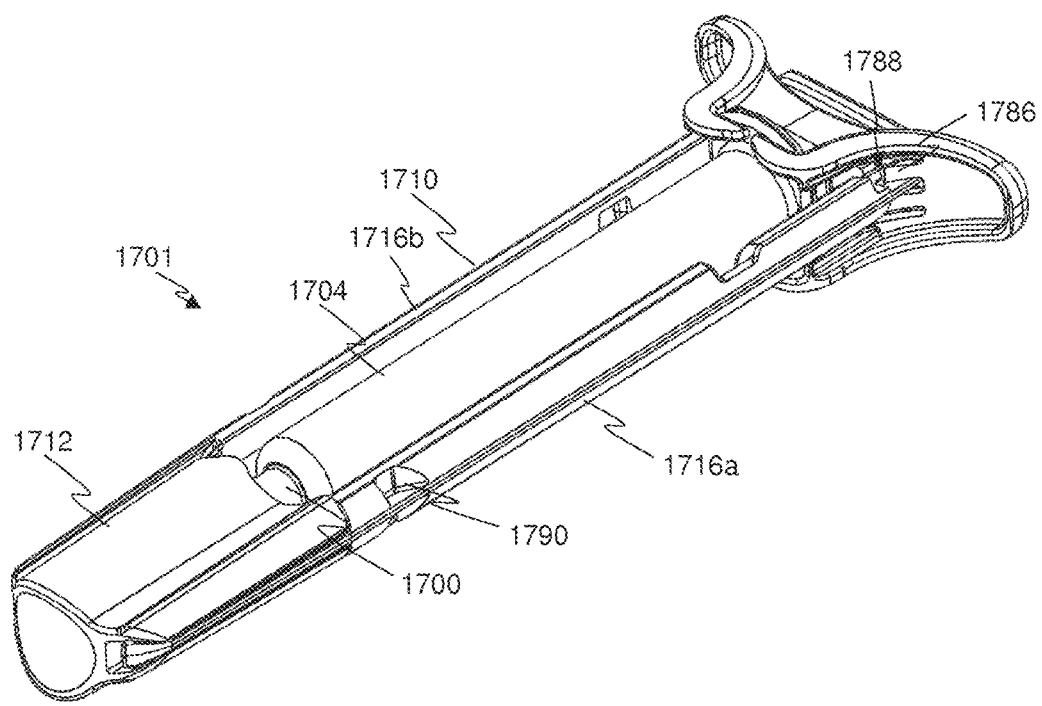
FIG. 17 shows a safety syringe comprising a locking mechanism.
Figure 18:
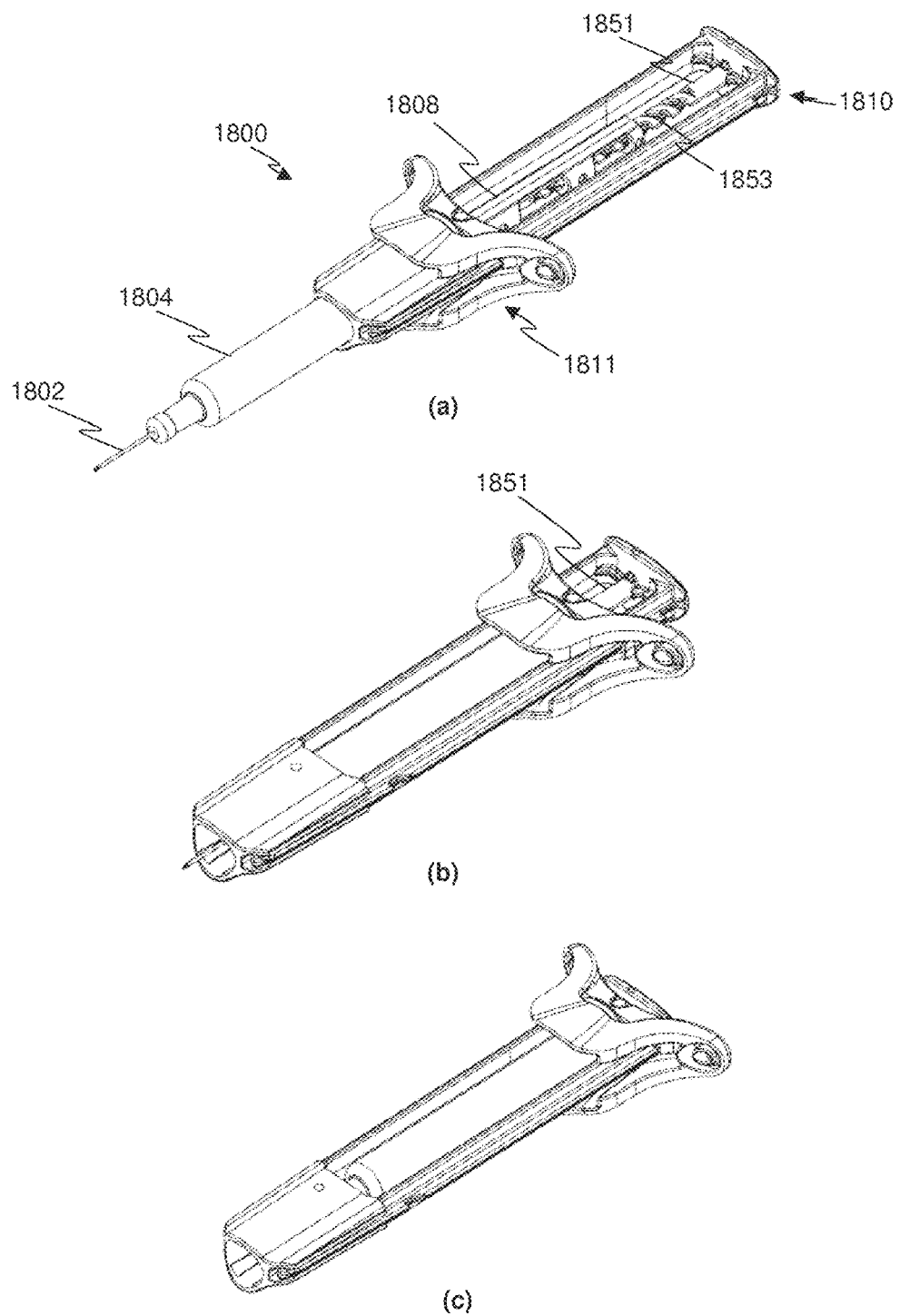
FIG. 18a is an isometric view of a safety syringe with a plunger in a first position along its inward stroke.
FIG. 18b is an isometric view of a safety syringe with a plunger in a second position along its inward stroke.
FIG. 18c is an isometric view of a safety syringe with a plunger at the end of its inward stroke.
Figure 20:
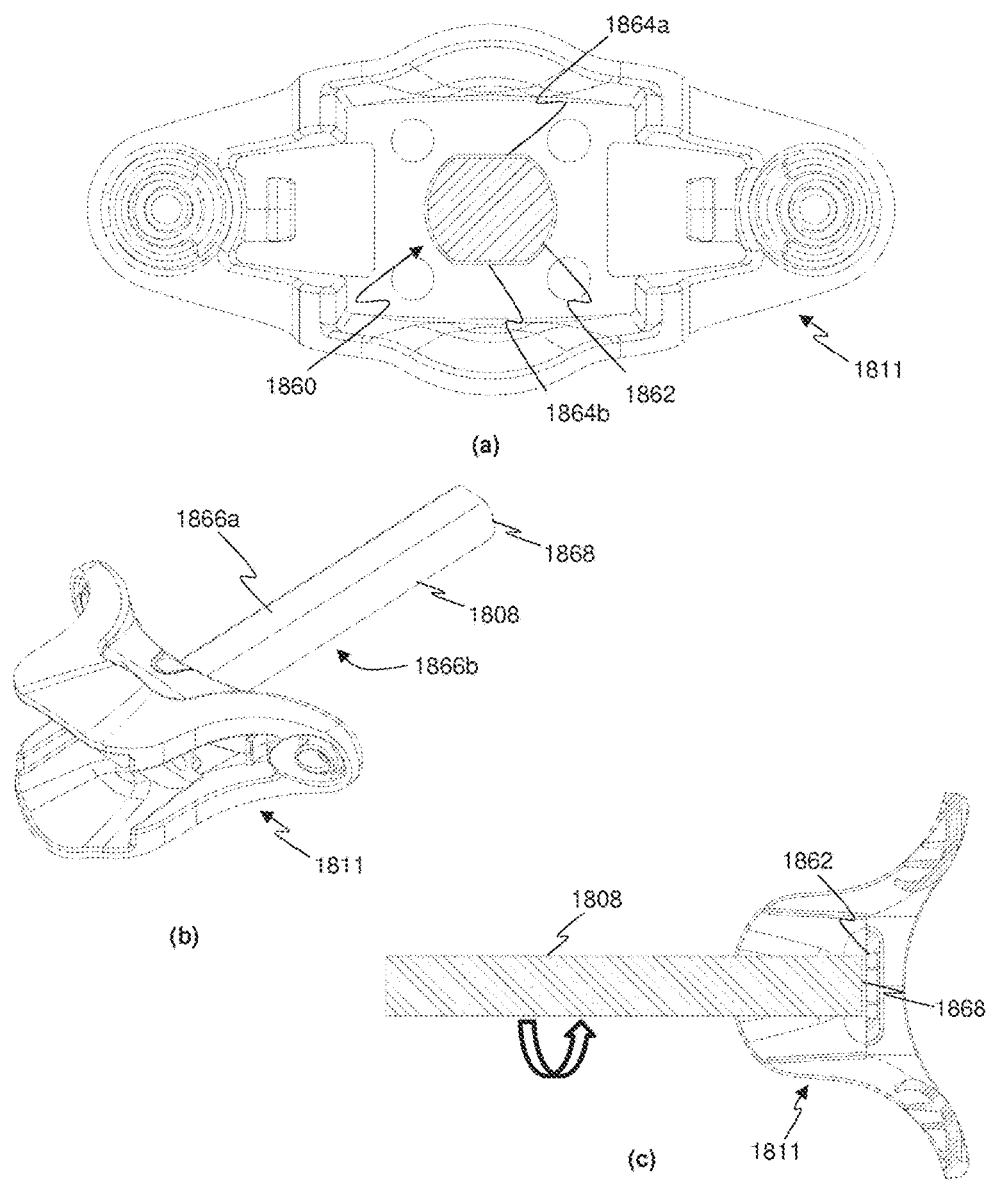
FIG. 20a is a plan view of a handle portion.
FIG. 20b is an isometric view of a handle portion and a syringe plunger.
FIG. 20c is a section through a handle portion and a syringe plunger.

FIG. 17 shows a safety syringe apparatus 1701 fitted to a syringe 1700 comprising a locking mechanism that comprises a projection 1786 configured to enter a locking recess 1788. Many of the features of the apparatus 1701 and syringe 1700 are similar to those described above in respect of any of the other exemplary apparatus. As such, a description of those features is not given again here and corresponding reference numerals are used to identify them in FIG. 17.

In the exemplary locking mechanism of FIG. 17, the projection is fixed in relation to a barrel 1704 of a syringe 1700 to which the safety syringe apparatus 1701 is fitted and the locking recess 1786 is located on the safety plunger 1710. It is noted that in other exemplary locking mechanisms, the projection 1786 may be located on the safety plunger 1710 and the locking recess 1788 may be fixed in relation to the barrel 1704. Further, one of the projection 1786 or the locking recess 1788 may be located on the sheath 1712 as opposed to the safety plunger 1710. There may be a plurality of projections and a plurality of locking recesses, as shown in FIG. 17.

The projection 1786 is urged towards the locking recess under a biasing force. In the exemplary locking mechanism of FIG. 17, the biasing force is provided by resilience in the projection 1786. That is, the projection 1786 is a resiliently deformable prong.

The projection 1786 is urged towards the locking recess 1788 and enters the locking recess 1788 when the locking recess 1788 and the projection 1786 are aligned. Before alignment, the projection 1786 rides along an outer surface of an arm 1716a, 1716b of the safety plunger 1710. The projection 1786 therefore exerts the biasing force against the outer surface of the arm 1716a, 1716b. This force against the arm 1716a, 1716b produces friction during travel of the safety plunger 1710 along its inward stroke and increases the force required by a user to move the safety plunger 1710 on its inward stroke. As the safety plunger 1710 is coupled to the syringe plunger, the force required to move the syringe plunger is also increased. The increase in required force may be considered to have a damping effect on the movement of the syringe plunger.

In exemplary apparatus comprising a lost motion device, such as the lost motion device 1009 shown in FIG. 10a, the damping of the movement of the syringe plunger may provide a benefit in reducing the likelihood of compressing the lost motion device at the beginning of the inward stroke of the syringe plunger. As explained above, the lost motion device may be included at an end of the syringe plunger in order to compensate for tolerances in manufacture of syringes. For this purpose, it is desirable that the lost motion device is compressed, as necessary, at the end of the inward stroke of the syringe plunger. However, if a large force is exerted on the safety plunger 1710 (and therefore the syringe plunger) then the resulting rapid build-up in pressure within the barrel 1704 of the syringe 1700 may compress the lost motion device, preventing it from compensating for manufacturing tolerances in the syringe 1700. By exerting a frictional force on the safety plunger 1710, the projection 1786 of the locking mechanism absorbs some of the force applied by the user to the safety plunger 1710 and therefore reduces the amount of force transferred to the liquid within the barrel 1704. As such, the pressure within the barrel does not increase as much and this reduces the likelihood that the lost motion device will compress early in the inward stroke of the syringe plunger.

A storage recess 1790 is formed in the safety plunger 1710 for accommodating the projection 1786 when the safety syringe apparatus 1701 is extended and in a state that it may be stored. The storage recess prevents deformation of the projection 1786 over long periods while the safety syringe apparatus 1701 is stored. This ensures the resilience of the projection 1786 is maintained.

Exemplary safety syringes disclosed herein may comprise rate controlling means for limiting and/or controlling (e.g. decreasing) a rate of extraction of the syringe needle from a subject. In particular exemplary safety syringes, the rate controlling means may be configured to limit and/or control the rate of depression of the safety plunger after decoupling from the syringe plunger. In exemplary safety syringes, the syringe needle is extracted from the subject by a force applied to the skin of the subject by the sheath resulting from pressure applied to the safety plunger after it is decoupled from the syringe plunger. Therefore, controlling and or limiting the rate of travel of the safety plunger after such decoupling can limit and/or control the rate of extraction of the syringe needle.

Such exemplary safety syringes limit discomfort felt by a subject as a result of too rapid an extraction of the syringe needle. Limiting the rate of extraction of the syringe needle also allows greater control of the safety syringe during extraction. If the rate of extraction is uncontrolled and therefore sudden then this can result in movement of the syringe around the injection site after extraction and may cause shock to the subject receiving the injection.

Referring to FIGS. 18a to 21c, exemplary safety syringes are shown that limit and/or control the rate of extraction of a syringe needle from a subject. FIGS. 18a-c and 19a-c show one exemplary safety syringe 1800, and FIGS. 20a-c and 21a-c show another exemplary safety syringe 2000. Many of the features of the safety syringes of FIGS. 18a-c and 19a-c are the same or similar to the features of other exemplary safety syringes described herein. Therefore, not all of the features of the safety syringes of FIGS. 18a-c and 19a-c are described here. The focus of the following description is on the features of the safety syringes that differ from features already described above. Other arrangements may be envisaged within the scope of the appended claims.

FIGS. 18a-c show perspective views of the safety syringe 1800 at different stages of operation. FIGS. 19a-c show sections through the safety syringe 1800 at corresponding stages of operation.

Referring to FIG. 18a, the safety syringe 1800 comprises a rate controlling means. The rate controlling means comprises a rate controlling member 1851 having a first screw thread 1853 and a corresponding second screw thread 1855 configured to engage the first screw thread 1853.

The rate controlling means is configured to limit and/or control the rate of extraction of a needle 1802 from a subject. The rate controlling member 1851 of FIG. 18a forms part of a safety plunger 1810 and is configured to engage with a syringe plunger 1808 and, specifically, the exemplary rate limiting member 1851 shown is configured to extend into the syringe plunger 1808. The engagement of the rate limiting member 1851 with the syringe plunger 1808 is configured to limit and/or control the rate of relative motion between the safety plunger 1810 and the syringe plunger 1808 after decoupling. In the exemplary safety syringe of FIG. 18a, the engagement between the rate limiting member 1851 and the syringe plunger 1808 is configured to limit and/or control the rate at which the rate limiting member 1851 is able to enter the syringe plunger 1808.

The rate limiting member 1851 comprises a screw thread 1853 configured to engage with a corresponding screw thread 1855 (shown in FIG. 19a) on the syringe plunger 1808.

While the safety plunger 1810 and the syringe plunger 1808 are coupled, as in FIGS. 18a and 19a, they travel together on application of a force to the safety plunger 1810.

FIGS. 18b and 19b show the point at which the safety plunger 1810 decouples from the syringe plunger 1808.

After decoupling, the safety plunger 1810 is free to move relative to the syringe plunger 1808 and, specifically, to move towards the needle end of the safety syringe 1800 while the syringe plunger 1808 remains substantially stationary, with respect to longitudinal movement. Upon the application of further force to the safety plunger 1810 after decoupling from the syringe plunger 1808, the rate limiting member 1851 begins to travel within the syringe plunger 1808, as shown in FIGS. 18c and 19c. The screw thread 1853 on the rate limiting member 1851 interacts with the screw thread 1855 in the syringe plunger 1808 to impart a rotational force. The rotational force causes the syringe plunger to rotate within a barrel 1804 of the safety syringe 1800.

The rotation of the syringe plunger 1808 within the barrel 1804 is resisted by a friction between a bung 1857 and an inner surface of the barrel 1804 and this limits and/or controls the rate of movement of the safety plunger 1810 after decoupling from the syringe plunger 1808.

The bung 1857 may be formed of a resiliently deformable material, such as a rubberised material, and has a diameter slightly larger than an internal diameter of the barrel 1804, such that a seal is formed when the bung 1857 is inserted within the barrel 1804. That seal may also provide resistance to the rotational motion of the syringe plunger 1808 within the barrel 1804. Alternatively or in addition, the screw threads 1853, 1855 may be configured to resist rotational motion of the syringe plunger 1808 for example by friction between the screw threads 1853, 1855 themselves. The interacting surfaces of the screw threads 1853, 1855 may be configured to provide a particular friction force. Alternatively or in addition, the syringe plunger 1808 may not be fixed to the bung 1857 and may be free to rotate therein. In such arrangements, at least part of the force resisting rotation of the syringe plunger 1808 may be provided by friction between the syringe plunger 1808 and the bung 1857.

FIG. 20*a* shows an end elevation of the handle portion 1811. FIG. 20*b* shows a perspective view of a syringe plunger 1808 partially passed through the handle portion 1811. FIG. 20*c* shows a section through a syringe plunger 1808 fully passed through a handle portion 1811. For clarity, FIGS. 20*a-c* do not show any other features of the safety syringe 1800.

In exemplary apparatus, the safety plunger 1810 may be coupled to the syringe plunger 1808 by a rotation prevention member 1860 configured to prevent rotation of the syringe plunger 1808 along at least part of its inward stroke. As rotation of the syringe plunger 1808 under the force applied to the rate limiting member 1851 (and in exemplary apparatus, the screw thread 1853) is prevented, the syringe plunger 1808 moves along its inward stroke under a force applied to the safety plunger 1810. The syringe plunger 1808 and the safety plunger 1810 are therefore coupled, as they move together on an inward (or outward) stroke.

In exemplary apparatus, the rotation prevention member 1860 may comprise a keyed aperture 1862 in a handle portion 1811 of the safety syringe 1800. The keyed aperture 1862 comprises keying features 1864*a-b* that correspond to keying features 1866*a-b* on the syringe plunger 1808, such that rotation of the syringe plunger 1808 is prevented when the keying features 1866*a-b* of the syringe plunger 1808 engage with the keying features 1864*a-b* of the handle portion 1811, as shown in FIG. 20*b*.

The syringe plunger 1808 decouples from the safety plunger 1810 when the syringe plunger 1808 is released from the rotation prevention member 1860. In exemplary apparatus, this may be provided by the keying features 1866*a-b* of the syringe plunger 1808 no longer engaging with the keying features 1864*a-b* of the handle portion 1811. For example, the syringe plunger 1808 may comprise keying features 1866*a-b* over only part of its length and once those keying features 1866*a-b* have passed through the aperture 1862, the syringe plunger 1808 may be free to rotate. Alternatively, and as shown in FIGS. 20*a-c*, a head 1868 of the syringe plunger 1808 may be configured such that it can pass through the aperture 1862. In exemplary syringe plungers 1808, the head 1868 may have the same cross section as the region of the syringe plunger 1808 comprising the keying features 1866*a-b*. Therefore, the syringe plunger 1808 is configured to pass through the aperture 1862 completely, as shown in FIG. 20*c*. When the syringe plunger 1808 has passed through the aperture 1862 the keying features 1866*a-b* of the syringe plunger 1808 are no longer engaged with the keying features 1864*a-b* of the aperture 1862 and the syringe plunger 1808 is free to rotate. At this point, the syringe plunger 1808 and the safety plunger 1810 are decoupled.

It is noted that the term "decoupled" as used herein encompasses any situation in which relative motion is permitted between a syringe plunger and a safety plunger. In specific apparatus, the relative motion may be relative longitudinal motion. This applies to all apparatus disclosed herein. That is, a syringe plunger does not need to be detached or separated from a safety plunger in order to be decoupled from it. Further, there may still be some movement of a safety plunger along its inward (or outward) stroke after decoupling, but there is a difference between a rate of movement between a safety plunger and a syringe plunger. For example, in the apparatus of FIGS. 18*a-c* and 19*a-c*, there may be some longitudinal movement of the syringe plunger along the inward stroke as well as rotational movement within the barrel after decoupling.

Figure 21:
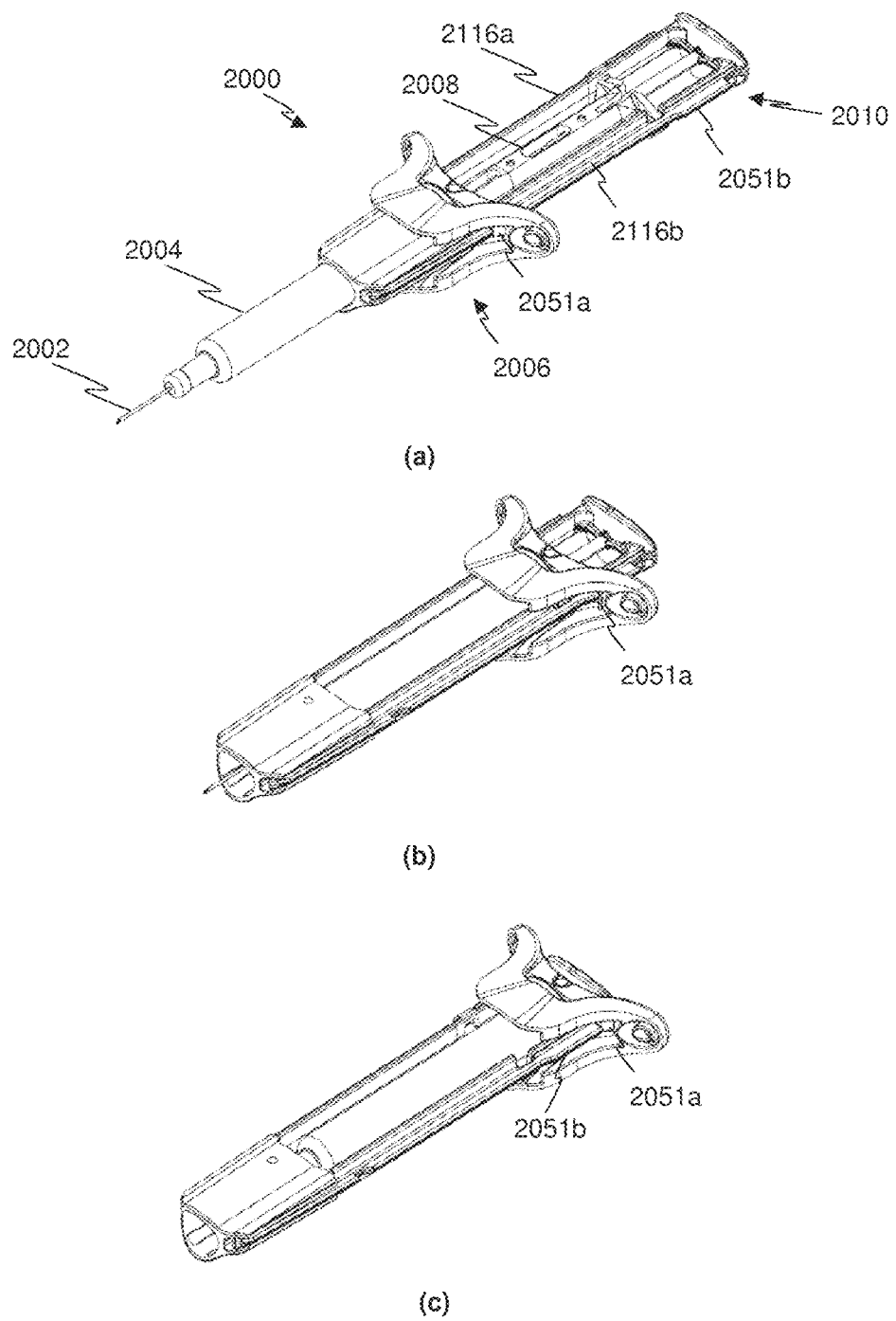
FIG. 21a is an isometric view of a safety syringe with a plunger in a first position along its inward stroke.
FIG. 21b is an isometric view of a safety syringe with a plunger in a second position along its inward stroke.
FIG. 21c is an isometric view of a safety syringe with a plunger at the end of its inward stroke.

Referring to FIG. 21, an exemplary safety syringe 2000 is shown and is configured to limit and/or control a rate of extraction of a needle 2002 from a subject after decoupling of a safety plunger 2010 and a syringe plunger 2008. The safety syringe comprises a rate controlling means 2051*a*, 2051*b* configured to limit and/or control a rate of travel of the safety plunger 2010 along its inward stroke after decoupling. The rate controlling means 2051*a*, 2051*b* comprises a resiliently deformable rate controlling projection 2051*a* and a deforming surface 2051*b*. The rate controlling projection 2051*a* is located on a handle portion 2006 and projects inwardly towards a longitudinal axis of the safety syringe 2000. The rate controlling projection 2051*a* may be the same or similar to the projection 1788 shown in FIG. 17.

The deforming surface 2051*b* is configured to deform the rate controlling projection 2051*a* as it passes over the deforming surface 2051*b*. In the exemplary safety syringe 2000, the deforming surface 2051*b* is located on the safety plunger 2010 and is configured to deform the rate controlling projection 2051*a* such that the force required to move the safety plunger 2010 along its inward stroke after decoupling is increased. In the exemplary safety syringe 2000 of FIGS. 21 and 22, the deforming surface comprises a tab extending outwardly away from the longitudinal axis of the safety syringe 2000. In the exemplary safety syringe 2000, a tab is located on each arm 2116*a*, 2116*b* of the safety plunger 2010. Each tab has a corresponding rate controlling projection 2051*a*. The tabs are positioned such that the rate controlling projections 2051*a* are deformed by the deforming surface 2051*b* after decoupling of the safety plunger 2010 from the syringe plunger 2008. In this way the rate of extraction of the needle 2002 from the subject may be controlled, e.g. decreased.

The operation of the safety syringe 2000 is now described with reference to FIGS. 22*a-c*. In FIG. 22*a*, the safety syringe 2000 is shown in the extended state and with the safety plunger 2010 and the syringe plunger 2008 coupled. The rate controlling projections 2051*a* are located in recesses 2059. This has the effect of locking the safety syringe 2000 in the extended state. The recesses 2059 are configured to prevent further extension of the safety syringe 2000 and also to require an initial force to overcome a threshold before an inward stroke of the safety plunger 2010 and the syringe plunger 2008 can begin.

After the threshold force is overcome, the rate controlling projections 2051a are deformed and the safety plunger 2010 and the syringe plunger 2008 begin to move along their inward strokes. At a point along the inward strokes, the safety plunger 2010 and the syringe plunger 2008 become decoupled, using any method discussed above.

In FIG. 22b, the safety syringe 2000 is shown shortly after decoupling and the rate controlling projections 2051a are shown in contact with the deforming surfaces 2051b. The rate controlling projections 2051a are further deformed by the deforming surfaces 2051b and therefore exert a force on the arms 2116a, 2116b of the safety plunger 2010 by way of the deforming surfaces 2051b. The increased force applied by the rate controlling projections 2051a on the arms 2116a, 2116b increases friction between the rate controlling projections 2051a and the deforming surfaces 2051b and the rate of extraction of the needle 2002 from the subject is thereby limited and/or controlled.

In FIG. 22c, the safety syringe 2000 has completed its inward stroke and the rate controlling projections 2051a have passed over the deforming surfaces 2051b and snapped back into locking recesses 2061 on the arms 2116a, 2116b. The locking recesses 2061 are configured to prevent the outward movement (i.e. extension) of the safety plunger 2010.

Exemplary safety syringes and safety syringe apparatus may be provided as a kit of parts for assembly. The kit of parts may comprise a plurality of elemental parts for assembly or may comprise a one or more composite parts (or sub-assemblies) that are pre-assembled.

Broadly, exemplary apparatus disclosed herein may comprise four parts: a safety plunger; a syringe plunger; a handle portion; and a sheath. These parts may be single moulded elements or may be constructed from a plurality of moulded elements. The four parts may be provided as one or more sub-assemblies.

For example, the safety plunger, syringe plunger and handle portion may be provided as a first sub-assembly. The first sub-assembly may be provided in a kit of parts with a sheath. In such configurations, a safety syringe may be assembled by positioning a pre-loaded syringe barrel into the first sub-assembly and then connecting the sheath to the first sub-assembly. Alternatively, the syringe barrel may be positioned within the sheath and the sheath may then be connected to the first sub-assembly.

In another example, the safety plunger and the syringe plunger may be provided as a second sub-assembly. The second sub assembly may be provided along with the handle portion and the sheath in a kit of parts. In such arrangements, the safety syringe may be assembled by connecting the second subassembly to the handle portion, positioning a pre-loaded syringe barrel into the handle portion and second sub-assembly and then connecting the sheath to the handle portion and second sub-assembly. Alternatively, the syringe barrel may be positioned within the sheath and the sheath may then be connected to the handle portion and the second sub-assembly.

In another example, each of the four parts may be supplied separately as a kit of parts. In such arrangements, the safety plunger, syringe plunger and handle portion may all be connected together. A pre-loaded syringe barrel may be connected to the assembled safety plunger, syringe plunger and handle portion, and the sheath may then be connected to the assembled safety plunger, syringe plunger and handle portion. Alternatively, the syringe barrel may be positioned within the sheath and the sheath may then be connected to the assembled safety plunger, syringe plunger and handle portion.

Various exemplary safety syringes described herein provide a locking means to lock the safety syringes in an extended state. The safety syringes may be supplied to a medical professional preloaded with a medicament and in the extended state. The locking means allows the medical professional to handle the safety syringe by the safety plunger and/or the syringe plunger, as the safety plunger and syringe plunger are prevented from further extension by the locking means.

The locking means also allows exemplary safety syringes to be auto-disabling. Such safety syringes may comprise a syringe plunger that is not physically connected to the bung. Rather, an end of the syringe plunger abuts the bung without being attached. In this configuration, the syringe plunger is able to push the bung into the barrel of the syringe in order to expel the contents of the barrel, but if the syringe plunger is withdrawn from the barrel it is disengaged from the bung, which is left in the barrel. Such safety syringes cannot be re-used, as the bung is trapped within the barrel and are therefore considered auto-disabling. The locking means provided on various exemplary safety syringes allows the auto-disabling feature, as the syringe plunger cannot be extended further than the locking means will permit and is therefore held in contact with the bung without needing to be secured to it.

It is noted that many of the features of the exemplary apparatus described above and shown in the drawings may be included in other exemplary apparatus. As such, the different drawings are not necessarily to be considered as separate embodiments and features from one drawing may be transferred to an apparatus in another drawing. It is also noted that any of the features of the safety syringes described herein may be used in a safety syringe apparatus for fitting to a syringe.

The skilled person will be able to envisage other safety syringes and features thereof without departing from the scope of the appended claims. In particular, it is noted that one or more features included in one or more drawings may be integrated into safety syringes shown in other drawings, as will be appreciated by the skilled person.

The invention claimed is:

1. A safety syringe comprising:
   a barrel having an opening at an end thereof;
   a syringe plunger configured to move within the barrel to cause a substance within the barrel to be expelled from the opening;
   a safety plunger coupled to the syringe plunger such that an inward stroke of the safety plunger causes the syringe plunger to move forward within the barrel; and
   a sheath configured to cover at least partially the opening in the barrel after use of the syringe,
   wherein the safety plunger is coupled to the sheath and is configured to decouple from the syringe plunger at a point on the inward stroke such that the safety plunger is moveable further forward independently of the syringe plunger,
   wherein the further forward movement of the safety plunger after decoupling of the safety plunger from the syringe plunger cause the sheath to move further forward to at least partially cover the opening fin the barrel,
   and wherein the safety syringe further comprises a rate controlling means for controlling a rate of travel of the safety plunger after decoupling, the rate controlling means comprising a rate limiting member coupled to the safety plunger and configured to engage with the syringe plunger, the rate limiting member comprising a first screw thread and the syringe plunger comprising a second screw thread that is configured to engage with the first screw thread to rotate the syringe plunger on the further forward movement of the safety plunger after decoupling of the safety plunger from the syringe plunger.

2. A safety syringe according to claim 1, wherein decoupling is substantially at a point at which the syringe plunger has reached the end of the barrel.

3. A safety syringe according to claim 1, further comprising a decoupling mechanism configured to decouple the safety plunger and the syringe plunger.

4. A safety syringe according to claim 3, wherein the decoupling mechanism is configured to decouple the safety plunger and the syringe plunger under rotation of the syringe plunger relative to the safety plunger.

5. A safety syringe according to claim 1, further comprising a locking mechanism configured to lock the sheath in a position at least partially covering the opening of the barrel.

6. A safety syringe according to claim 1, further comprising a rotation prevention member configured to prevent rotation of the syringe plunger before decoupling.

7. A safety syringe according to claim 6, wherein the rotation prevention member comprises an aperture through which the syringe plunger passes, wherein the aperture comprises first keying features configured to correspond to second keying features on the syringe plunger.

8. A safety syringe according to claim 7, wherein the syringe plunger is configured such that the second keying features disengage from the first keying features to decouple the syringe plunger from the safety plunger.

9. A safety syringe according to claim 7, wherein the syringe plunger is configured to pass through the aperture completely when the syringe plunger is decoupled from the safety plunger.

10. A safety syringe according to claim 1, further comprising a resiliently deformable bung within the barrel and configured to rotate when the syringe plunger rotates, wherein the bung has a diameter greater than an inner diameter of the barrel, such that a friction force resists rotation of the bung and the syringe plunger.

11. A safety syringe according to claim 1, further comprising a resiliently deformable bung within the barrel and configured to allow relative rotation between the resiliently deformable bung and the syringe plunger, and wherein a friction force between the syringe plunger and the resiliently deformable bung resists rotation of the bung and the syringe plunger.

12. A safety syringe according to claim 1, wherein the rate controlling means comprises a resiliently deformable rate controlling projection configured to be deformed by a deforming surface after decoupling, thereby generating a friction force resisting further movement of the safety plunger.

13. A safety syringe according to claim 1, wherein the safety plunger comprises a head and at least one arm that connects the head to the sheath such that the safety plunger and sheath move together, the head of the safety plunger for applying force by a user to cause the inward stroke of the safety plunger.

14. A safety syringe according to claim 1, further comprising a hypodermic needle connected to the opening in the barrel, and wherein the sheath is configured to cover at least partially the hypodermic needle after use of the syringe.

15. The safety syringe according to claim 1, wherein,
the safety plunger comprises a head and at least one arm that connects the head to the sheath, the head of the safety plunger being configured for applying force by a user to cause, via the at least one arm, the inward stroke of the safety plunger, and
the safety syringe further comprises a handle portion fixed in relation to the barrel, the handle portion comprises a main body and flanges extending laterally from the main body,
the flanges are configured to receive fingers of a user while a thumb applies a force to the head of the safety plunger, and
the at least one arm of the safety plunger is configured to pass through the handle portion such that during the safety plunger's inward stroke, i) the at least one arm of the safety plunger moves relative to the handle portion and the barrel with the sheath traveling along an outside of the barrel during the inward stroke of the safety plunger until the sheath at least partially covers the opening of the barrel, and ii) at an innermost point of the inward stroke of the safety plunger, a distal end of the sheath is beyond a distal end of the opening of the barrel such that the opening of the barrel is not exposed.

16. The safety syringe according to claim 1, wherein,
the safety plunger comprises a head and a pair of arms that directly connect the head to an end of the sheath such that, prior to decoupling, the safety plunger and sheath move together, the head of the safety plunger being configured for applying force by a user to cause, via the pair of arms, the inward stroke of the safety plunger, and
the safety syringe further comprises a handle portion fixed to the barrel, the handle portion comprises a main body and flanges extending laterally from the main body,
the flanges are configured to receive fingers of a user while the user applies a force to the head of the safety plunger, and
the pair of arms are configured to pass through the handle portion such that, during the inward stroke of the safety plunger, i) the safety plunger moves relative to the handle portion and the barrel, with the sheath traveling along an outside of the barrel during the inward stroke of the safety plunger until the sheath at least partially covers the opening of the barrel, and at an innermost point of the stroke of the safety plunger, a distal end of the sheath is beyond a distal end of the opening of the barrel, such that the opening of the barrel is not exposed.

17. A safety syringe apparatus for use with a syringe, the syringe comprising a barrel having an opening at an end thereof and a syringe plunger configured to move within the barrel to cause a substance within the barrel to be expelled from the opening, wherein the safety syringe apparatus comprises:
a safety plunger configured to be coupled to the syringe plunger such that an inward stroke of the safety plunger causes the syringe plunger to move forward within the barrel; and
a sheath configured to cover at least partially the opening in the barrel after use of the syringe,
wherein the safety plunger is coupled to the sheath and is configured to decouple from the syringe plunger at a point on the inward stroke such that the safety plunger is moveable further forward independently of the syringe plunger, wherein the safety plunger is configured such that the further forward movement of the safety plunger after decoupling of the safety plunger from the syringe plunger cause the sheath to move further forward to at least partially cover the opening fin the barrel, and wherein the safety plunger further comprises a rate limiting member forming part of a rate controlling means for controlling a rate of travel of the safety plunger after decoupling, the rate limiting member being configured to engage with the syringe plunger after decoupling and comprising a first screw thread configured to engage a second screw thread on the syringe plunger to rotate the syringe plunger on the further forward movement of the safety plunger after decoupling of the safety plunger from the syringe plunger.

18. A kit of parts comprising:

a safety plunger configured to be coupled to a syringe plunger of a syringe such that an inward stroke of the safety plunger causes the syringe plunger to move forward within the barrel; and a sheath configured to cover at least partially an opening in a barrel of the syringe after use of the syringe, wherein the safety plunger is configured to be coupled to the sheath and is configured to decouple from the syringe plunger at a point on the inward stroke such that the safety plunger is moveable further forward independently of the syringe plunger, wherein the further forward movement of the safety plunger after decoupling of the safety plunger from the syringe plunger cause the sheath to move further forward to at least partially cover the opening fin the barrel, and wherein the safety plunger further comprises a rate limiting member forming part of a rate controlling means for controlling a rate of travel of the safety plunger after decoupling, the rate limiting member being configured to engage with the syringe plunger after decoupling and comprising a first screw thread configured to engage a second screw thread on the syringe plunger to rotate the syringe plunger on the further forward movement of the safety plunger after decoupling of the safety plunger from the syringe plunger.

19. A kit of parts according to claim 18 further comprising a handle portion configured to be coupled to the barrel and to receive the safety plunger, such that the safety plunger is able to pass through the handle portion.

20. A kit of parts according to claim 18, further comprising the syringe plunger.

21. A kit of parts according to claim 18, further comprising the syringe.

* * * * *